United States Patent
Yu et al.

(10) Patent No.: US 6,689,579 B1
(45) Date of Patent: *Feb. 10, 2004

(54) POLYNUCLEOTIDES ENCODING NEUTROKINE-α

(75) Inventors: Guo-Liang Yu, Berkeley, CA (US); Reinhard Ebner, Gaithersburg, MD (US); Jian Ni, Germantown, MD (US)

(73) Assignee: Human Genome Sciences, Inc., Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/005,874

(22) Filed: Jan. 12, 1998

Related U.S. Application Data

(63) Continuation-in-part of application No. PCT/US96/17957, filed on Oct. 25, 1996.
(60) Provisional application No. 60/036,100, filed on Jan. 14, 1997.

(51) Int. Cl.[7] .......................... C12P 21/02; C12N 15/09; C12N 5/00; C07K 14/00; C07H 21/04
(52) U.S. Cl. ................... 435/69.1; 435/70.1; 435/252.3; 435/320.1; 435/325; 530/300; 530/350; 530/351; 536/23.1; 536/23.5
(58) Field of Search ............................... 536/23.5, 23.1; 435/69.1, 69.5, 252.3, 320.1, 70.1, 325; 530/300, 350, 351, 399

(56) References Cited

FOREIGN PATENT DOCUMENTS

| EP | 98302526 | | 4/1998 |
|---|---|---|---|
| EP | 0869180 | | 10/1998 |
| EP | 98309632 | | 11/1998 |
| EP | 921194 A2 | | 6/1999 |
| WO | 9733902 | * | 9/1997 |
| WO | WO 98/18921 A1 | | 5/1998 |
| WO | 9827114 | | 12/1998 |
| WO | WO 98/55620 A1 | | 12/1998 |
| WO | WO 98/55621 A1 | | 12/1998 |
| WO | 9911791 | * | 3/1999 |
| WO | WO 99/12694 A2 | | 3/1999 |
| WO | WO 99/33980 A2 | | 7/1999 |
| WO | WO 00/45836 A1 | | 8/2000 |
| WO | WO 00/50597 A2 | | 8/2000 |

OTHER PUBLICATIONS

Ferguson et al, *Hum. Mal. Genet* 6, 1997, p. 1589–94 (see attaches sequence alignment only).*
Skolnick et al. From genes to protein structure and function: novel applications of computational approaches in the genomic era. Trends in Biotech 18(1):34–39, 2000.*
Bork, A. Powers and pitfalls in sequence analysis: the 70% hurdle. Genome Res. 10: 398–400, 2000.*
Doerks et al. Protein annotation: detective work for function prediction. Trends in Genetics 14(6): 248–250, 1998.*
Smith et al. The challenges of genome sequence annotation or "The devil is in the details", Nature Biotech 15: 1222–1223, 1997.*
Brenner, S.E. Errors in genome function. Trends in Genetics 15(4):132–133, 1999.*
Bork et al. Go hunting in sequence databases but watch out for the traps. Trends in Genetics. 12(10):425–427, 1996.*
Wells, J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Elgert, K. Immunology: Understanding the Immune System, Wiley–Liss: New York, 1996, p. 24.*
Cheema et al., Elevated Serum B Lymphocyte Stimulator Levels in Patients with Systemic Immune–Based Rheumatic Diseases, *Arthritis and Rheumatism* (2001) 44:1313–1319.
U.S. patent application Ser. No. 60/041,797, SmithKline Beecham, Priority Document of EP 869180.
U.S. patent application Ser. No. 08/984,396, SmithKline Beecham, Priority Document of EP 869180.
U.S. patent application Ser. No. 60/068,959, Chiron, Priority Document of WO 99/33980.
U.S. patent application Ser. No. 60/048,776, Regeneron, Priority Document of 98/55620 & 98/55621.
U.S. patent application Ser. No. 60/066,386, Regeneron, Priority Document of 98/55620 & 98/55621.
U.S. patent application Ser. No. 60/033,601, Schering, Priority Document of WO 98/27114.
U.S. patent application Ser. No. 60/058,786, Biogen, Priority Document of 99/12964.
U.S. patent application Ser. No. 60/066,577, Eli Lilly, Priority Document of EP 921194.
U.S. patent application Ser. No. 60/096,173, Eli Lilly, Priority Document of EP 921194.

(List continued on next page.)

*Primary Examiner*—Elizabeth Kemmerer
*Assistant Examiner*—Bridget E. Bunner
(74) *Attorney, Agent, or Firm*—Human Genome Sciences, Inc.

(57) ABSTRACT

The present invention relates to a novel Neutrokine-α protein which is a member of the TNF protein family. In particular, isolated nucleic acid molecules are provided encoding the human Neutrokine-α protein including soluble forms of the extracellular domain. Neutrokine-α polypeptides are also provided as are vectors, host cells and recombinant methods for producing the same. The invention further relates to screening methods for identifying agonists and antagonists of Neutrokine-α activity. Also provided are diagnostic methods for detecting immune system-related disorders and therapeutic methods for treating immune system-related disorders.

194 Claims, 9 Drawing Sheets

OTHER PUBLICATIONS

Moore et al., BlyS: Member of the Tumor Necrosis Factor Family and B Lymphocyte Stimulator, Science, (1999) 285:260–263.

Mackay et al., Mice Transgenic for BAFF Develop Lympyhocytic Disorders Along with Autoimmune Manifestations, J. Exp. Med., (1999) 190:1697–1710.

Thompson et al., BAFF Binds to the Tumor Necrosis Factor Receptor–like Molecule B Cell Maturation Antigen and Is Important for Maintaining the Peripheral B Cell Population, J. Exp. Med., (2000) 192:129–135.

Xia et al., TACI Is a TRAF–interacting Receptor for TALL–1, a Tumor Necrosis Factor Family Member Involved in B Cell Regulation, J. Exp. Med., (2000) 192:137–143.

Yan et al., Identification of a receptor for BlyS demonstrates a crucial role in humoral immunity, Nature Immunology, (2000) 1:37–41.

Cyster, Jason G., Marginal zone B cells may steal the limelight as the roles of Pyk–2 and BlyS begin to be elucidated. Pyk–2 deficiency leads to their loss whereas signaling via the BlyS receptor may augment their function, Nature Immunology, (2000) 1:9–10.

Marsters, et al., Interaction of the TNF homologues BlyS and April with the TNF receptor homologues BCMA and TACI, Current Biology, (2000) 10:785–788.

Hatzoglou et al., TNF Receptor Family Member BCMA (B Cell Maturation) Associates with TNF Receptor–Associated Factor (TRAF) 1, TRAF2, TRAF3 and Activates NF–κB, Elk–1, c–Jun N–Terminal Kinase, and p38 Mitogen–Activated Protein Kinase, The Journal of Immunology, (2000) 165:1322–1330.

Gross et al.; TACI and BCMA are receptors for a TNF homologue implicated in B–cell autoimmune disease, Letters to Nature, (2000) 404:995–999.

Schneider et al., BAFF, a Novel Ligand of the Tumor Necrosis Factor Family, Stimulates B Cell Growth, J. Exp. Med., (1999) 189:1747–1756.

Do et al., Attenuation of Apoptosis Underlies B Lymphocyte Stimulator Enhancement of Humoral Immune Response, J. Exp. Med., (2000) 192:953–964.

Khare et al., Severe B Cell Hyperplasia and autoimmune disease in TALL–1 transgenic mice, PNAS, (2000) 97:3370–3375.

Yan et al., Identification of a receptor for BlyS demonstrates a crucial role in humoral immunity, Nature Immunology, (2000) 1:37–41.

Yu et al., APRIL and TALL–1 and receptors BCMA and TAC1: system for regulating humoral immunity, (2000) 1:252–256.

Nardelli et al., Synthesis and release of B–lymphocyte stimulator from myeloid cells, Immunobiology, (2001) 97:198–204.

Baumgarth, Nicole, Secreted lgM versus BlyS in germinal center formation, Nature Immunology, (2000) 1:179.

Zhang et al., Cutting Edge: A Role for B Lymphocyte Stimulator in Systemic Lupus Erythematosus, The Journal of Immunology, (2001) 166:6–10.

Wu et al., Tumor Necrosis Factor (TNF) Receptor Superfamily Member TACI Is a High Affinity Receptor for TNF Family Members APRIL and BlyS, The Journal of Biological Chemistry (2000) 275:34578–34585.

Parry et al., Pharmacokinetics and Immunological Effects of Exogenously administered Recombinant Human B Lymphocyte Stimulator (BlyS) in Mice, The Journal of Pharmacology and Experimental Therapies, (2001) 296:396–404.

Kanakaraj et al., BLys Binds to B Cells With High Affinity and Induces Activation of the Transcription Factors NF–κB and Elf–1, Cytokine (2001) 13:25–31.

Laabi et al., Lymphocyte Survival—Ignorance is BlyS, Science Magazine, (2001) 289:883.

GenBank Accession No. G30081 (Oct. 4, 1996).
GenBank Accession No. AA682496 (Dec. 19, 1997).
GenBank Accession No. AA166695 (Nov. 9, 1997).
GenBank Accession No. AA906714 (Jun. 9, 1998).
GenBank Accession No. R16882 (Apr. 14, 1995).
GenBank Accession No. T87299 (Mar. 17, 1995).
GenBank Accession No. D79690 (Feb. 9, 1996).
GenBank Accession No. DAI182472 (Oct. 8, 1998).
GenBank Accession No. AA422749 (Oct. 16, 1997).
GenBank Accession No. R16934 (Apr. 14, 1995).

* cited by examiner

1   AAATTCAGGATAACTCTCCTGAGGGGTGAGCCAAGCCCTGCCATGTAGTGCACGCAGGAC

61  ATCAACAAACACAGATAACAGGAAATGATCCATTCCCTGTGGTCACTTATTCTAAAGGCC

121 CCAACCTTCAAAGTTCAAGTAGTGATATGGATGACTCCACAGAAAGGGAGCAGTCACGCC
1                                   M   D   D   S   T   E   R   E   Q   S   R   L

181 TTACTTCTTGCCTTAAGAAAAGAGAAGAAATGAAACTGAAGGAGTGTGTTTCCATCCTCC
13   T   S   C   L   K   K   R   E   E   M   K   L   K   E   C   V   S   I   L   P

241 CACGGAAGGAAAGCCCCTCTGTCCGATCCTCCAAAGACGGAAAGCTGCTGGCTGCAACCT
33   R   K   E   S   P   S   V   R   S   S   K   D   G   K   L   L   A   A   T   L

301 TGCTGCTGGCACTGCTGTCTTGCTGCCTCACGGTGGTGTCTTTCTACCAGGTGGCCGCCC
53   L   L   A   L   L   S   C   C   L   T   V   V   S   F   Y   Q   V   A   A   L

361 TGCAAGGGGACCTGGCCAGCCTCCGGGCAGAGCTGCAGGGCCACCACGCGGAGAAGCTGC
73   Q   G   D   L   A   S   L   R   A   E   L   Q   G   H   H   A   E   K   L   P

421 CAGCAGGAGCAGGAGCCCCCAAGGCCGGCCTGGAGGAAGCTCCAGCTGTCACCGCGGGAC
93   A   G   A   G   A   P   K   A   G   L   E   E   A   P   A   V   T   A   G   L

481 TGAAAATCTTTGAACCACCAGCTCCAGGAGAAGGCAACTCCAGTCAGAACAGCAGAAATA
113  K   I   F   E   P   P   A   P   G   E   G   N   S   S   Q   N   S   R   N   K

541 AGCGTGCCGTTCAGGGTCCAGAAGAAACAGTCACTCAAGACTGCTTGCAACTGATTGCAG
133  R   A   V   Q   G   P   E   E   T   V   T   Q   D   C   L   Q   L   I   A   D

FIG.1A

```
601  ACAGTGAAACACCAACTATACAAAAAGGATCTTACACATTTGTTCCATGGCTTCTCAGCT
153   S  E  T  P  T  I  Q  K  G  S  Y  T  F  V  P  W  L  L  S  F

661  TTAAAAGGGGAAGTGCCCTAGAAGAAAAAGAGAATAAAATATTGGTCAAAGAAACTGGTT
173   K  R  G  S  A  L  E  E  K  E  N  K  I  L  V  K  E  T  G  Y

721  ACTTTTTTATATATGGTCAGGTTTTATATACTGATAAGACCTACGCCATGGGACATCTAA
193   F  F  I  Y  G  Q  V  L  Y  T  D  K  T  Y  A  M  G  H  L  I

781  TTCAGAGGAAGAAGGTCCATGTCTTTGGGGATGAATTGAGTCTGGTGACTTTGTTTCGAT
213   Q  R  K  K  V  H  V  F  G  D  E  L  S  L  V  T  L  F  R  C

841  GTATTCAAAATATGCCTGAAACACTACCCAATAATTCCTGCTATTCAGCTGGCATTGCAA
233   I  Q  N  M  P  E  T  L  P  N  N  S  C  Y  S  A  G  I  A  K

901  AACTGGAAGAAGGAGATGAACTCCAACTTGCAATACCAAGAGAAAATGCACAAATATCAC
253   L  E  E  G  D  E  L  Q  L  A  I  P  R  E  N  A  Q  I  S  L

961  TGGATGGAGATGTCACATTTTTTGGTGCATTGAAACTGCTGTGACCTACTTACACCATGT
273   D  G  D  V  T  F  F  G  A  L  K  L  L

1021 CTGTAGCTATTTTCCTCCCTTTCTCTGTACCTCTAAGAAGAAAGAATCTAACTGAAAATA

1081 CCAAAAAAAAAAAAAAAAAA
```

```
162  S V Q T K V N - - L L S A I K S P C Q R E T P E - - - G A E A    TNFalpha
141  Q Y P F H V P - - L L S Q K M V Y P - - - - - - - - - L Q        TNFbeta
169  A V G P T P E L L E G A E T V T P V L D P A R R Q G Y G          LTbeta
217  K Y P Q D L V - - M M E G K M M S Y C - - - - - - T T G          FASL
223  E L S - - L V T L F R C I Q N M P E T L P N - - - - - -          Neutrokine alpha 188  K P W Y E P I Y L G G V F Q L E K G D R L S A E I N R P D Y      TNFalpha
161  E P W L H S M Y H G A A F Q L T Q G D Q L S T H T D G I P H      TNFbeta
199  P L W Y T S V G F G G L V Q L R R G E R V Y V N I S H P D M      LTbeta
237  Q M W A R S S Y L G A V F N L T S A D H L Y V N V S E L S L      FASL
243  - - - N S C Y S A G I A K L E E G D E L Q L A I P R E N A        Neutrokine alpha 218  L D F A E S G Q V Y F G I I A L                                  TNFalpha
191  L V L S P S - T V F F G A F A L                                  TNFbeta
229  V D F A R - G K T F F G A V M V G                                LTbeta
267  V N F E S - Q T F F G L Y K L                                    FASL
269  Q I S L D G D V T F F G A L K L L                                Neutrokine alpha
```

FIG.2C

```
            1                                                    50
HSOAD55R    .........A GGNTAACTCT CCTGAGGGGT GAGCCAAGCC CTGCCATGTA
HNEDU15X    ...AAATTCA GGATAACTCT CCTGAGGGGT GAGCCAAGCC CTGCCATGTA
HSLAH84R    .AATTCGGCA NAGNAAACTG GTTACTTTTT TATATATGGT CAGGTTTTAT
HLTBM08R    AATTCGGCAC GAGCAAGGCC GGCCTGGAGG AAGCTCCAGC TGTCACCGCG 51                                                   100
HSOAD55R    GTGCACGCAG GACATCANCA A..ACACANN NNNCAGGAAA TAATCCATTC
HNEDU15X    GTGCACGCAG GACATCAACA A..ACACAGA TAACAGGAAA TGATCCATTC
HSLAH84R    ATACTGATAA GACCTACGCC ATGGGACATC TAGTTCAGAG GAAGAAGGTC
HLTBM08R    GGACTGAAAA TCTTTGAACC ACCAGCTCCA GGAGAAGGCA ACTCCAGTCA 101                                                  150
HSOAD55R    CCTGTGGTCA CTTATTCTAA AGGCCCCAAC CTTCAAAGTT CAAGTAGTGA
HNEDU15X    CCTGTGGTCA CTTATTCTAA AGGCCCCAAC CTTCAAAGTT CAAGTAGTGA
HSLAH84R    CATGTCTTTG GGGATGAATT GAGTCTGGTG ACTTTGTTTC GATGTATTCA
HLTBM08R    GAACAGCAGA AATAAGCGTG CCGTTCAGGG TCCAGAAGAA ACAGTCACTC 151                                                  200
HSOAD55R    TATGGATGAC TCCACAGAAA GGGAGCAGTC ACGCCTTACT TCTTGCCTTA
HNEDU15X    TATGGATGAC TCCACAGAAA GGGAGCAGTC ACGCCTTACT TCTTGCCTTA
HSLAH84R    AAATATGCCT GAAACACTAC CCAATAATTC CTGCTATTCA GCTGGCATTG
HLTBM08R    AAGACTGCTT GCAACTGNTT GCAGACAGTG AAACACCAAC TATACAAAAA 201                                                  250
HSOAD55R    AGAAAAGAGA AGAAATGAAA CTGNAAGGAG TGTGTTTCCA TCCTCCCACG
HNEDU15X    AGAAAAGAGA AGAAATGAAA CT.GAAGGAG TGTGTTTCCA TCCTCCCACG
HSLAH84R    CAAAACTGGN AGGAAGGA.. ...GATGAAC TCCAACTTGC AATACCAGGG
HLTBM08R    GGCTCCCTTC TGNTGCCACA TTTGGGCCAA GGAATGGAGA GATTTCTTCG 251                                                  300
HSOAD55R    GAAGGAAAGC CCCTCTNTCC GATCCTCCAA AGACGGAAAG CTGCTGGCTG
HNEDU15X    GAAGGAAAGC CCCTCTGTCC GATCCTCCAA AGACGGAAAG CTGCTGGCTG
HSLAH84R    GAAAATGCAC AATTATCACT GGGATGGAGA TGTTCACATT TTTTGGGTGC
HLTBM08R    TCTGGAAACA TTTTGCCAAA CTCTTCAGAT ACTCTTTNCT CTCTGGGAAT 301                                                  350
HSOAD55R    CAACCTTGNT GNTGGCATTG TGTTCTTGCT GNCTCAAGGT GGTGTTNTT.
HNEDU15X    CAACCTTGCT GCTGGCACTG CTGTCTTGCT GCCTCACGGT GGTGTCTTTC
HSLAH84R    CATTGAAACT GCTGTGACCT NCTTACANCA NGTGCTGTTN GCTATTTTNC
HLTBM08R    CAAAGGAAAA TCTCTACTTA GATTNACACA TTTGTTCCCA TGGGTNTCTT 351                                                  400
HSOAD55R    .......... .......... .......... .......... ..........
HNEDU15X    TACCAGGTGG CCGCCCTGCA AGGGGACCTG GCCAGCCTCC GGGCAGAGCT
HSLAH84R    CTNCCTNTTC TNTGGTAACC TCTTAGGAAG GAAGGATTCT TAACTGGGAA
HLTBM08R    AAGTTTTAAA AGGGGAGTGC CCTTAGGAGG AAAAGGGGAT AAATATTGGC
```

FIG.4A

```
                401                                                       450
HSOAD55R    ..........  ..........  ..........  ..........  ..........
HNEDU15X    GCAGGGCCAC  CACGCGGAGA  AGCTGCCAGC  AGGAGCAGGA  GCCCCCAAGG
HSLAH84R    ATAACCCAAA  AAAANNTTAA  ANGGGTANGN  GNNANANGNG  GGGNNGTTNN
HLTBM08R    CAAGGNACTG  GTTANTTTNT  AAATATGGTC  AGGTTTNTAT  ANCTGGTAGG 451                                                       500
HSOAD55R    ..........  ..........  ..........  ..........  ..........
HNEDU15X    CCGGCCTGGA  GGAAGCTCCA  GCTGTCACCG  CGGGACTGAA  AATCTTTGAA
HSLAH84R    CNNGNNGNNT  TTTNGGNNTA  TNTTNTNNTN  GGGNNNNGTA  AAAATGGGGC
HLTBM08R    CCTCGCCATG  GGCATTNATT  CANGGNGAGG  NCNNTCTTTT  GGGNTGA...

501                                                       550
HSOAD55R    ..........  ..........  ..........  ..........  ..........
HNEDU15X    CCACCAGCTC  CAGGAGAAGG  CAACTCCAGT  CAGAACAGCA  GAAATAAGCG
HSLAH84R    CNANGGGGGN  TTTTT.....  ..........  ..........  ..........
HLTBM08R    ..........  ..........  ..........  ..........  ..........

551                                                       600
HSOAD55R    ..........  ..........  ..........  ..........  ..........
HNEDU15X    TGCCGTTCAG  GGTCCAGAAG  AAACAGTCAC  TCAAGACTGC  TTGCAACTGA
HSLAH84R    ..........  ..........  ..........  ..........  ..........
HLTBM08R    ..........  ..........  ..........  ..........  ..........

601                                                       650
HSOAD55R    ..........  ..........  ..........  ..........  ..........
HNEDU15X    TTGCAGACAG  TGAAACACCA  ACTATACAAA  AAGGATCTTA  CACATTTGTT
HSLAH84R    ..........  ..........  ..........  ..........  ..........
HLTBM08R    ..........  ..........  ..........  ..........  ..........

651                                                       700
HSOAD55R    ..........  ..........  ..........  ..........  ..........
HNEDU15X    CCATGGCTTC  TCAGCTTTAA  AAGGGGAAGT  GCCCTAGAAG  AAAAAGAGAA
HSLAH84R    ..........  ..........  ..........  ..........  ..........
HLTBM08R    ..........  ..........  ..........  ..........  ..........

701                                                       750
HSOAD55R    ..........  ..........  ..........  ..........  ..........
HNEDU15X    TAAAATATTG  GTCAAAGAAA  CTGGTTACTT  TTTTATATAT  GGTCAGGTTT
HSLAH84R    ..........  ..........  ..........  ..........  ..........
HLTBM08R    ..........  ..........  ..........  ..........  ..........

751                                                       800
HSOAD55R    ..........  ..........  ..........  ..........  ..........
HNEDU15X    TATATACTGA  TAAGACCTAC  GCCATGGGAC  ATCTAATTCA  GAGGAAGAAG
HSLAH84R    ..........  ..........  ..........  ..........  ..........
HLTBM08R    ..........  ..........  ..........  ..........  ..........
```

FIG. 4B

|           | 801        |            |            |            | 850        |
|-----------|------------|------------|------------|------------|------------|
| HSOAD55R  | .......... | .......... | .......... | .......... | .......... |
| HNEDU15X  | GTCCATGTCT | TTGGGGATGA | ATTGAGTCTG | GTGACTTTGT | TTCGATGTAT |
| HSLAH84R  | .......... | .......... | .......... | .......... | .......... |
| HLTBM08R  | .......... | .......... | .......... | .......... | .......... |

|           | 851        |            |            |            | 900        |
|-----------|------------|------------|------------|------------|------------|
| HSOAD55R  | .......... | .......... | .......... | .......... | .......... |
| HNEDU15X  | TCAAAATATG | CCTGAAACAC | TACCCAATAA | TTCCTGCTAT | TCAGCTGGCA |
| HSLAH84R  | .......... | .......... | .......... | .......... | .......... |
| HLTBM08R  | .......... | .......... | .......... | .......... | .......... |

|           | 901        |            |            |            | 950        |
|-----------|------------|------------|------------|------------|------------|
| HSOAD55R  | .......... | .......... | .......... | .......... | .......... |
| HNEDU15X  | TTGCAAAACT | GGAAGAAGGA | GATGAACTCC | AACTTGCAAT | ACCAAGAGAA |
| HSLAH84R  | .......... | .......... | .......... | .......... | .......... |
| HLTBM08R  | .......... | .......... | .......... | .......... | .......... |

|           | 951        |            |            |            | 1000       |
|-----------|------------|------------|------------|------------|------------|
| HSOAD55R  | .......... | .......... | .......... | .......... | .......... |
| HNEDU15X  | AATGCACAAA | TATCACTGGA | TGGAGATGTC | ACATTTTTTG | GTGCATTGAA |
| HSLAH84R  | .......... | .......... | .......... | .......... | .......... |
| HLTBM08R  | .......... | .......... | .......... | .......... | .......... |

|           | 1001       |            |            |            | 1050       |
|-----------|------------|------------|------------|------------|------------|
| HSOAD55R  | .......... | .......... | .......... | .......... | .......... |
| HNEDU15X  | ACTGCTGTGA | CCTACTTACA | CCATGTCTGT | AGCTATTTTC | CTCCCTTTCT |
| HSLAH84R  | .......... | .......... | .......... | .......... | .......... |
| HLTBM08R  | .......... | .......... | .......... | .......... | .......... |

|           | 1051       |            |            |            | 1100       |
|-----------|------------|------------|------------|------------|------------|
| HSOAD55R  | .......... | .......... | .......... | .......... | .......... |
| HNEDU15X  | CTGTACCTCT | AAGAAGAAAG | AATCTAACTG | AAAATACCAA | AAAAAAAAAA |
| HSLAH84R  | .......... | .......... | .......... | .......... | .......... |
| HLTBM08R  | .......... | .......... | .......... | .......... | .......... |

|           | 1101       |
|-----------|------------|
| HSOAD55R  | ......     |
| HNEDU15X  | AAAAAA     |
| HSLAH84R  | ......     |
| HLTBM08R  | ......     |

FIG.4C

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 1100 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 147..1001

(ix) FEATURE:
        (A) NAME/KEY: sig_peptide
        (B) LOCATION: 285..381

(ix) FEATURE:
        (A) NAME/KEY: mat_peptide
        (B) LOCATION: 147..1001

(xi) SEQUENCE DESCRIPTION: SEQ ID NO:1:

```
AAATTCAGGA TAACTCTCCT GAGGGGTGAG CCAAGCCCTG CCATGTAGTG CACGCAGGAC         60

ATCAACAAAC ACAGATAACA GGAAATGATC CATTCCCTGT GGTCACTTAT TCTAAAGGCC        120
CCAACCTTCA AAGTTCAAGT AGTGAT ATG GAT GAC TCC ACA GAA AGG GAG CAG        173
                             Met Asp Asp Ser Thr Glu Arg Glu Gln
                               1               5

TCA CGC CTT ACT TCT TGC CTT AAG AAA AGA GAA GAA ATG AAA CTG AAG         221
Ser Arg Leu Thr Ser Cys Leu Lys Lys Arg Glu Glu Met Lys Leu Lys
 10              15                  20                  25

GAG TGT GTT TCC ATC CTC CCA CGG AAG GAA AGC CCC TCT GTC CGA TCC         269
Glu Cys Val Ser Ile Leu Pro Arg Lys Glu Ser Pro Ser Val Arg Ser
                 30                  35                  40

TCC AAA GAC GGA AAG CTG CTG GCT GCA ACC TTG CTG CTG GCA CTG CTG         317
Ser Lys Asp Gly Lys Leu Leu Ala Ala Thr Leu Leu Leu Ala Leu Leu
             45                  50                  55

TCT TGC TGC CTC ACG GTG GTG TCT TTC TAC CAG GTG GCC GCC CTG CAA         365
Ser Cys Cys Leu Thr Val Val Ser Phe Tyr Gln Val Ala Ala Leu Gln
         60                  65                  70

GGG GAC CTG GCC AGC CTC CGG GCA GAG CTG CAG GGC CAC CAC GCG GAG         413
Gly Asp Leu Ala Ser Leu Arg Ala Glu Leu Gln Gly His His Ala Glu
     75                  80                  85

AAG CTG CCA GCA GGA GCA GGA GCC CCC AAG GCC GGC TGA GAA GCT             461
Lys Leu Pro Ala Gly Ala Gly Ala Pro Lys Ala Gly Leu Glu Glu Ala
```

```
                90                  95                 100                 105
        CCA GCT GTC ACC GCG GGA CTG AAA ATC TTT GAA CCA CCA GCT CCA GGA        509
        Pro Ala Val Thr Ala Gly Leu Lys Ile Phe Glu Pro Pro Ala Pro Gly
                            110                 115                 120

GAA GGC AAC TCC AGT CAG AAC AGC AGA AAT AAG CGT GCC GTT CAG GGT        557
        Glu Gly Asn Ser Ser Gln Asn Ser Arg Asn Lys Arg Ala Val Gln Gly
                        125                 130                 135

CCA GAA GAA ACA GTC ACT CAA GAC TGC TTG CAA CTG ATT GCA GAC AGT        605
        Pro Glu Glu Thr Val Thr Gln Asp Cys Leu Gln Leu Ile Ala Asp Ser
                    140                 145                 150

GAA ACA CCA ACT ATA CAA AAA GGA TCT TAC ACA TTT GTT CCA TGG CTT        653
        Glu Thr Pro Thr Ile Gln Lys Gly Ser Tyr Thr Phe Val Pro Trp Leu
                155                 160                 165

CTC AGC TTT AAA AGG GGA AGT GCC CTA GAA GAA AAA GAG AAT AAA ATA        701
        Leu Ser Phe Lys Arg Gly Ser Ala Leu Glu Glu Lys Glu Asn Lys Ile
        170                 175                 180                 185

TTG GTC AAA GAA ACT GGT TAC TTT TTT ATA TAT GGT CAG GTT TTA TAT        749
        Leu Val Lys Glu Thr Gly Tyr Phe Phe Ile Tyr Gly Gln Val Leu Tyr
                        190                 195                 200

ACT GAT AAG ACC TAC GCC ATG GGA CAT CTA ATT CAG AGG AAG AAG GTC        797
        Thr Asp Lys Thr Tyr Ala Met Gly His Leu Ile Gln Arg Lys Lys Val
                    205                 210                 215

CAT GTC TTT GGG GAT GAA TTG AGT CTG GTG ACT TTG TTT CGA TGT ATT        845
        His Val Phe Gly Asp Glu Leu Ser Leu Val Thr Leu Phe Arg Cys Ile
                220                 225                 230

CAA AAT ATG CCT GAA ACA CTA CCC AAT AAT TCC TGC TAT TCA GCT GGC        893
        Gln Asn Met Pro Glu Thr Leu Pro Asn Asn Ser Cys Tyr Ser Ala Gly
        235                 240                 245

ATT GCA AAA CTG GAA GAA GGA GAT GAA CTC CAA CTT GCA ATA CCA AGA        941
        Ile Ala Lys Leu Glu Glu Gly Asp Glu Leu Gln Leu Ala Ile Pro Arg
        250                 255                 260                 265

GAA AAT GCA CAA ATA TCA CTG GAT GGA GAT GTC ACA TTT TTT GGT GCA        989
        Glu Asn Ala Gln Ile Ser Leu Asp Gly Asp Val Thr Phe Phe Gly Ala
                        270                 275                 280

TTG AAA CTG CTG TGACCTACTT ACACCATGTC TGTAGCTATT TTCCTCCCTT          1041
        Leu Lys Leu Leu
                285

TCTCTGTACC TCTAAGAAGA AAGAATCTAA CTGAAAATAC CAAAAAAAAA AAAAAAAA            1100

(2) INFORMATION FOR SEQ ID NO:2:

(i) SEQUENCE CHARACTERISTICS:
            (A) LENGTH: 285 amino acids
            (B) TYPE: amino acid
            (D) TOPOLOGY: linear (ii) MOLECULE TYPE: protein (xi) SEQUENCE DESCRIPTION: SEQ ID NO:2:

Met Asp Asp Ser Thr Glu Arg Glu Gln Ser Arg Leu Thr Ser Cys Leu
 1               5                  10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80
```

```
Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
            115                 120                 125

Ser Arg Asn Lys Arg Ala Val Gln Gly Pro Glu Glu Thr Val Thr Gln
        130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
            195                 200                 205

Gly His Leu Ile Gln Arg Lys Lys Val His Val Phe Gly Asp Glu Leu
        210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

(2) INFORMATION FOR SEQ ID NO:3:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Ser Thr Glu Ser Met Ile Arg Asp Val Glu Leu Ala Glu Glu Ala
1                5                  10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Ser Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140
```

```
Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230
```

(2) INFORMATION FOR SEQ ID NO:4:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Thr Pro Pro Glu Arg Leu Phe Leu Pro Arg Val Cys Gly Thr Thr
1               5                   10                  15

Leu His Leu Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
        50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Pro Ser Ser Pro
            115                 120                 125

Leu Tyr Leu Ala His Glu Val Gln Leu Phe Ser Ser Gln Tyr Pro Phe
            130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205
```

(2) INFORMATION FOR SEQ ID NO:5:

(i) SEQUENCE CHARACTERISTICS:
        (A) LENGTH: 244 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly
```

(2) INFORMATION FOR SEQ ID NO:6:

(i) SEQUENCE CHARACTERISTICS:
        (A) LENGTH: 281 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80
```

```
Leu Cys Leu Leu Val Met Phe Phe Met Val Leu Val Ala Leu Val Gly
                85                  90                  95
Leu Gly Leu Gly Met Phe Gln Leu Phe His Leu Gln Lys Glu Leu Ala
            100                 105                 110
Glu Leu Arg Glu Ser Thr Ser Gln Met His Thr Ala Ser Ser Leu Glu
        115                 120                 125
Lys Gln Ile Gly His Pro Ser Pro Pro Glu Lys Lys Glu Leu Arg
    130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
            180                 185                 190
Ser Lys Val Tyr Phe Arg Gly Gln Ser Cys Asn Asn Leu Pro Leu Ser
        195                 200                 205
His Lys Val Tyr Met Arg Asn Ser Lys Tyr Pro Gln Asp Leu Val Met
    210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
                245                 250                 255
Leu Tyr Val Asn Val Ser Glu Leu Ser Leu Val Asn Phe Glu Glu Ser
            260                 265                 270
Gln Thr Phe Phe Gly Leu Tyr Lys Leu
        275                 280
```

(2) INFORMATION FOR SEQ ID NO:7:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
AGGNTAACTC TCCTGAGGGG TGAGCCAAGC CCTGCCATGT AGTGCACGCA GGACATCANC    60
AAACACANNN NNCAGGAAAT AATCCATTCC CTGTGGTCAC TTATTCTAAA GGCCCCAACC   120
TTCAAAGTTC AAGTAGTGAT ATGGATGACT CCACAGAAAG GGAGCAGTCA CGCCTTACTT   180
CTTGCCTTAA GAAAAGAGAA GAAATGAAAC TGNAAGGAGT GTGTTTCCAT CCTCCCACGG   240
AAGGAAAGCC CCTCTNTCCG ATCCTCCAAA GACGGAAAGC TGCTGGCTGC AACCTTGNTG   300
NTGGCATTGT GTTCTTGCTG NCTCAAGGTG GTGTTNTT                           338
```

(2) INFORMATION FOR SEQ ID NO:8:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
AATTCGGCAN AGNAAACTGG TTACTTTTTT ATATATGGTC AGGTTTTATA TACTGATAAG    60
```

-continued

| | | |
|---|---|---|
| ACCTACGCCA TGGGACATCT AGTTCAGAGG AAGAAGGTCC ATGTCTTTGG GGATGAATTG | 120 |
| AGTCTGGTGA CTTTGTTTCG ATGTATTCAA AATATGCCTG AAACACTACC CAATAATTCC | 180 |
| TGCTATTCAG CTGGCATTGC AAAACTGGNA GGAAGGAGAT GAACTCCAAC TTGCAATACC | 240 |
| AGGGGAAAAT GCACAATTAT CACTGGGATG GAGATGTTCA CATTTTTTGG GTGCCATTGA | 300 |
| AACTGCTGTG ACCTNCTTAC ANCANGTGCT GTTNGCTATT TTNCCTNCCT NTTCTNTGGT | 360 |
| AACCTCTTAG GAAGGAAGGA TTCTTAACTG GGAAATAACC CAAAAAAANN TTAAANGGGT | 420 |
| ANGNGNNANA NGNGGGGNNG TTNNCNNGNN GNNTTTTNGG NNTATNTTNT NNTNGGGNNN | 480 |
| NGTAAAAATG GGGCCNANGG GGGNTTTTT | 509 |

(2) INFORMATION FOR SEQ ID NO:9:

(i) SEQUENCE CHARACTERISTICS:
        (A) LENGTH: 497 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | | |
|---|---|---|
| AATTCGGCAC GAGCAAGGCC GGCCTGGAGG AAGCTCCAGC TGTCACCGCG GGACTGAAAA | 60 |
| TCTTTGAACC ACCAGCTCCA GGAGAAGGCA ACTCCAGTCA GAACAGCAGA AATAAGCGTG | 120 |
| CCGTTCAGGG TCCAGAAGAA ACAGTCACTC AAGACTGCTT GCAACTGNTT GCAGACAGTG | 180 |
| AAACACCAAC TATACAAAAA GGCTCCCTTC TGNTGCCACA TTTGGGCCAA GGAATGGAGA | 240 |
| GATTTCTTCG TCTGGAAACA TTTTGCCAAA CTCTTCAGAT ACTCTTTNCT CTCTGGGAAT | 300 |
| CAAAGGAAAA TCTCTACTTA GATTNACACA TTTGTTCCCA TGGGTNTCTT AAGTTTTAAA | 360 |
| AGGGGAGTGC CCTTAGGAGG AAAAGGGGAT AAATATTGGC CAAGGNACTG GTTANTTTNT | 420 |
| AAATATGGTC AGGTTTNTAT ANCTGGTAGG CCTCGCCATG GGCATTNATT CANGGNGAGG | 480 |
| NCNNTCTTTT GGGNTGA | 497 |

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

| | |
|---|---|
| GTGGGATCCA GCCTCCGGGC AGAGCTG | 27 |

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| | |
|---|---|
| GTGAAGCTTT TATTACAGCA GTTTCAATGC ACC | 33 |

(2) INFORMATION FOR SEQ ID NO:12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GTGTCATGAG CCTCCGGGCA GAGCTG                                              26

(2) INFORMATION FOR SEQ ID NO:13:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GTGAAGCTTT TATTACAGCA GTTTCAATGC ACC                                      33

(2) INFORMATION FOR SEQ ID NO:14:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

GTGGGATCCC CGGGCAGAGC TGCAGGGC                                            28

(2) INFORMATION FOR SEQ ID NO:15:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

GTGGGATCCT TATTACAGCA GTTTCAATGC ACC                                      33

(2) INFORMATION FOR SEQ ID NO:16:

(i) SEQUENCE CHARACTERISTICS:
            (A) LENGTH: 129 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

GCGGGATCCG CCACCATGAA CTCCTTCTCC ACAAGCGCCT TCGGTCCAGT TGCCTTCTCC          60

CTGGGGCTGC TCCTGGTGTT GCCTGCTGCC TTCCCTGCCC CAGTTGTGAG ACAAGGGGAC         120

CTGGCCAGC                                                                129

(2) INFORMATION FOR SEQ ID NO:17:

```
     (i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:17:

GTGGGATCCT TACAGCAGTT TCAATGCACC                                            30
```

POLYNUCLEOTIDES ENCODING NEUTROKINE-α

This application claims the benefit of priority under 35 U.S.C. §119(e) of U.S. Provisional Application No. 60/036,100, filed Jan. 14, 1997 and this application is also is a continuation-in-part of, and claims the benefit of priority under 35 U.S.C. §120 of, International Patent Application No. PCT/US96/17957, filed Oct. 25, 1996. Both U.S. Provisional Application No. 60/036,100 and International Patent Application No. PCT/US96/17957 are hereby incorporated by reference.

FIELD OF THE INVENTION

The present invention relates to a novel cytokine expressed by neutrophils which has therefore been designated Neutrokine-α protein ("Neutrokine-α"). In particular, isolated nucleic acid molecules are provided encoding the Neutrokine-α protein. Neutrokine-α polypeptides are also provided, as are vectors, host cells and recombinant methods for producing the same.

RELATED ART

Human tumor necrosis factors (TNF-α) and (TNF-β, or lymphotoxin) are related members of a broad class of polypeptide mediators, which includes the interferons, interleukins and growth factors, collectively called cytokines (Beutler, B. and Cerami, A., *Annu. Ret,. Immunol.*, 7:625–655 (1989)). Sequence analysis of cytokine receptors has defined several subfamilies of membrane proteins (1) the Ig superfamily, (2) the hematopoietin (cytokine receptor superfamily and (3) the tumor necrosis factor (TNF)/nerve growth factor (NGF) receptor superfamily (for review of TNF superfamily see, Gruss and Dower, *Blood* 85(12):3378–3404 (1995) and Aggarwal and Natarajan, *Eur. Cytokine Netw.*, 7(2):93–124 (1996)). The TNF/NGF receptor superfamily contains at least 10 difference proteins. Gruss and Dower, supra. Ligands for these receptors have been identified and belong to at least two cytokine superfamilies. Gruss and Dower, supra.

Tumor necrosis factor (a mixture of TNF-α and TNF-β) was originally discovered as a result of its anti-tumor activity, however, now it is recognized as a pleiotropic cytokine capable of numerous biological activities including apoptosis of some transformed cell lines, mediation of cell activation and proliferation and also as playing important roles in immune regulation and inflammation.

To date, known members of the TNF-ligand superfamily include TNF-α, TNF-β (lymphotoxin-α), LT-β, OX40L, Fas ligand, CD30L, CD27L, CD40L and 4-IBBL. The ligands of the TNF ligand superfamily are acidic, TNF-like molecules with approximately 20% sequence homology in the extracellular domains (range, 12%–36%) and exist mainly as membrane-bound forms with the biologically active form being a trimeric/multimeric complex. Soluble forms of the TNF ligand superfamily have only been identified so far for TNF, LT-β, and Fas ligand (for a general review, see Gruss, H. and Dower, S. K., *Blood*, 85(12):3378–3404 (1995)), which is hereby incorporated by reference in its entirety. These proteins are involved in regulation of cell proliferation, activation, and differentiation, including control of cell survival or death by apoptosis or cytotoxicity (Armitage, R. J., *Curr. Opin. Immunol.* 6:407 (1994) and Smith, C. A., *Cell* 75:959 (1994)).

Tumor necrosis factor-alpha (TNF-α; also termed cachectin; hereinafter "TNF") is secreted primarily by monocytes and macrophages in response to endotoxin or other stimuli as a soluble homotrimer of 17 kD protein subunits (Smith, R. A. et al., *J. Biol. Chem.* 262:6951–6954 (1987)). A membrane-bound 26 kD precursor form of TNF has also been described (Kriegler, M. et al., *Cell* 53:45–53 (1988)).

Accumulating evidence indicates that TNF is a regulatory cytokine with pleiotropic biological activities. These activities include: inhibition of lipoprotein lipase synthesis ("cachectin" activity) (Beutler, B. et al., *Nature* 316:552 (1985)), activation of polymorphonuclear leukocytes (Klebanoff, S. J. et al., *J. Immunol.* 136:4220 (1986); Perussia, B., et al., *J. Immunol.* 138:765 (1987)), inhibition of cell growth or stimulation of cell growth (Vilcek, J. et al., *J. Exp. Med.* 163:632 (1986); Sugarman, B. J. et al., *Science* 230:943 (1985); Lachman, L. B. et al.,*J. Immunol.* 138:2913 (1987)), cytotoxic action on certain transformed cell types (Lachman, L. B. et al., supra; Darzynkiewicz, Z. et al., *Canc. Res.* 44:83 (1984)), antiviral activity (Kohase, M. et al., *Cell* 45:659 (1986); Wong, G. H. W. et al., *Nature* 323:819 (1986)), stimulation of bone resorption (Bertolini, D. R. et al., *Nature* 319:516 (1986); Saklatvala, J., *Nature* 322:547 (1986)), stimulation of collagenase and prostaglandin E2 production (Dayer, J.-M. et al., *J. Exp. Med.* 162:2163 (1985)); and immunoregulatory actions, including activation of T cells (Yokota, S. et al.,*J. Immunol.* 140:531 (1988)), B cells (Kehrl, J. H. et al., *J. Exp. Med.* 166:786 (1987)), monocytes (Philip, R. et al, *Nature* 323:86 (1986)), thymocytes (Ranges, G. E. et al., *J. Exp. Med.* 167:1472 (1988)), and stimulation of the cell-surface expression of major histocompatibility complex (MHC) class I and class II molecules (Collins, T. et al., *Proc. Natl. Acad. Sci. USA* 83:446 (1986); Pujol-Borrel, R. et al., *Nature* 326:304 (1987)).

TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)).

Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al.,*J. Exp. Med.* 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al. *J. Parent. Enter. Nutr.* 12:286–298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., *Br. J. Surg.* 76:670–671 (1989); Debets, J. M. H. et al.,*Second Vienna Shock Forum*, p.463–466 (1989); Simpson, S. Q. et al, *Crit. Care Clin.* 5:27–47 (1989)), including fever, malaise, anorexia, and cachexia. Endotoxin is a potent monocyte/macrophage activator which stimulates production and secretion of TNF (Kornbluth, S. K. et al., *J. Immunol.* 137:2585–2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin (Michie, H. R. et al., *N. Eng. J. Med.* 318:1481–1486 (1988)). Endotoxin administration to human volunteers produces acute illness with flu-like symptoms including fever, tachycardia, increased metabolic rate and stress hormone release (Revhaug, A. et al., *Arch. Surg.* 123:162–170 (1988)). Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Med.* 17:489–497 (1989); Calandra, T. et al, *J. Infec. Dis.* 161:982–987 (1990)).

Passive immunotherapy directed at neutralizing TNF may have a beneficial effect in Gram-negative sepsis and endotoxemia, based on the increased TNF production and elevated TNF levels in these pathology states, as discussed above. Antibodies to a "modulator" material which was characterized as cachectin (later found to be identical to TNF) were disclosed by Cerami et al. (EPO Patent Publication 0,212,489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., *Allergy* 16:178 (1967); Kawasaki, T., *Shonica (Pediatrics)* 26:935 (1985)) were said to contain elevated TNF levels which were related to progress of the pathology (Yone et al., supra).

Other investigators have described mAbs specific for recombinant human TNF which had neutralizing activity in vitro (Liang, C-M. et al. *Biochem. Biophys. Res. Comm.* 137:847–854 (1986); Meager, A. et al., *Hybridoma* 6:305–311 (1987); Fendly et al., *Hybridoma* 6:359–369 (1987); Bringman, T S et al., *Hybridoma* 6:489–507 (1987); Hirai, M. et al., *J. Immunol. Meth.* 96:57–62 (1987); Moller, A. et al. (*Cytokine* 2:162–169 (1990)). Some of these mAbs were used to map epitopes of human TNF and develop enzyme immunoassays (Fendly et al., supra; Hirai et al., supra; Moller et al., supra) and to assist in the purification of recombinant TNF (Bringman et al., supra). However, these studies do not provide a basis for producing TNF neutralizing antibodies that can be used for in vivo diagnostic or therapeutic uses in humans, due to immunogenicity, lack of specificity and/or pharmaceutical suitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, J. C. et al., *J. Clin. Invest.* 81:1925–1937 (1988); Beutler, B. et al., *Science* 229:869–871 (1985); Tracey, K. J. et al., *Nature* 330:662–664 (1987); Shimamoto, Y. et al, *Immunol. Lett.* 17:311–318 (1988); Silva, A. T. et al., *J. Infect. Dis.* 162:421–427 (1990); Opal, S. M. et al., *J. Infect. Dis.* 161:1148–1152 (1990); Hinshaw, L. B. et al., *Circ. Shock* 30:279–292 (1990)).

To date, experience with anti-TNF mAb therapy in humans has been limited but shows beneficial therapeutic results, e.g., in arthritis and sepsis. See, e.g., Elliott, M. J. et al., *Baillieres Clin. Rheumatol.* 9:633–52 (1995); Feldmann M, et al., *Ann. N.Y. Acad. Sci. USA* 766:272–8 (1995); van der Poll, T. et al., *Shock* 3:1–12 (1995); Wherry et al., *Crit. Care. Med.* 21:S436–40 (1993); Tracey K. J., et al., *Crit. Care Med.* 21:S415–22 (1993).

Mammalian development is dependent on both the proliferation and differentiation of cells as well as programmed cell death which occurs through apoptosis (Walker, et al., *Methods Achiev. Exp. Pathol.* 13:18 (1988). Apoptosis plays a critical role in the destruction of immune thymocytes that recognize self antigens. Failure of this normal elimination process may play a role in autoimmune diseases (Gammon et al., *Immunology Today* 12:193 (1991)).

Itoh et al. (*Cell* 66:233 (1991)) described a cell surface antigen, Fas/CD23 that mediates apoptosis and is involved in clonal deletion of T-cells. Fas is expressed in activated T-cells, B-cells, neutrophils and in thymus, liver, heart and lung and ovary in adult mice (Watanabe-Fukunaga et al., *J. Immunol.* 148:1274 (1992)) in addition to activated T-cells, B-cells, neutorophils. In experiments where a monoclonal Ab is cross-linked to Fas, apoptosis is induced (Yonehara et al., *J. Exp. Med.* 169:1747 (1989); Trauth et al., *Science* 245:301 (1989)). In addition, there is an example where binding of a monoclonal Ab to Fas is stimulatory to T-cells under certain conditions (Alderson et al., *J. Exp. Med.* 178:2231 (1993)).

Fas antigen is a cell surface protein of relative MW of 45 Kd. Both human and murine genes for Fas have been cloned by Watanabe-Fukunaga et al., (*J. Immunol.* 148:1274 (1992)) and Itoh et al. (*Cell* 66:233 (1991)). The proteins encoded by these genes are both transmembrane proteins with structural homology to the Nerve Growth Factor/Tumor Necrosis Factor receptor superfamily, which includes two TNF receptors, the low affinity Nerve Growth Factor receptor and CD40, CD27, CD30, and OX40.

Recently the Fas ligand has been described (Suda et al., *Cell* 75:1169 (1993)). The amino acid sequence indicates that Fas ligand is a type II transmembrane protein belonging to the TNF family. Thus, the Fas ligand polypeptide comprises three main domains: a short intracellular domain at the amino terminal end and a longer extracellular domain at the carboxy terminal end, connected by a hydrophobic transmembrane domain. Fas ligand is expressed in splenocytes and thymocytes, consistent with T-cell mediated cytotoxicity. The purified Fas ligand has a MW of 40 kD.

Recently, it has been demonstrated that Fas/Fas ligand interactions are required for apoptosis following the activation of T-cells (Ju et al., *Nature* 373:444 (1995); Brunner et al., *Nature* 3 73:441 (1995)). Activation of T-cells induces both proteins on the cell surface. Subsequent interaction between the ligand and receptor results in apoptosis of the cells. This supports the possible regulatory role for apoptosis induced by Fas/Fas ligand interaction during normal immune responses.

Accordingly, there is a need to provide cytokines similar to TNF that are involved in pathological conditions. Such novel cytokines could be used to make novel antibodies or other antagonists that bind these TNF-like cytokines for therapy of disorders related to TNF-like cytokines.

SUMMARY OF THE INVENTION

The present invention provides isolated nucleic acid molecules comprising a polynucleotide encoding a cytokine that is structurally similar to TNF and related cytokines and is believed to have similar biological effects and activities. This cytokine is named Neutrokine-α and the invention includes Neutrokine-α polypeptides having at least a portion of the amino acid sequence in FIGS. 1A and 1B (SEQ ID NO:2) or amino acid sequence encoded by the cDNA clone deposited in a bacterial host on Oct. 22, 1996 assigned ATCC number 97768. The nucleotide sequence determined by sequencing the deposited Neutrokine-α clone, which is shown in FIGS. 1A and 1B (SEQ ID NO:1), contains an open reading frame encoding a complete polypeptide of 285 amino acid residues including an N-terminal methionine, a predicted intracellular domain of about 46 amino acid residues, a predicted transmembrane domain of about 26 amino acids, a predicted extracellular domain of about 213 amino acids, and a deduced molecular weight for the complete protein of about 31 kDa. As for other type II transmembrane proteins, soluble forms of Neutrokine-α include all or a portion of the extracellular domain cleaved from the transmembrane domain and a polypeptide comprising the complete Neutrokine-α polypeptide lacking the transmembrane domain, i.e., the extracellular domain linked to the intracellular domain.

Thus, one aspect of the invention provides an isolated nucleic acid molecule comprising a polynucleotide having a nucleotide sequence selected from the group consisting of: (a) a nucleotide sequence encoding a full-length Neutrokine-α polypeptide having the complete amino acid sequence in FIGS. 1A and 1B (SEQ ID NO:2) or as encoded by the cDNA clone contained in the ATCC Deposit of Oct. 22, 1996 ATCC Number 97768; (b) a nucleotide sequence encoding the predicted extracellular domain of the Neutrokine-α polypeptide having the amino acid sequence at positions 73 to 285 in FIGS. 1A and 1B (SEQ ID NO:2) or as encoded by the cDNA clone contained in ATCC No. 97768 deposited on Oct. 22, 1996; (c) a nucleotide sequence encoding a polypeptide comprising the Neutrokine-α intracellular domain (amino acid residues from about 1 to about 46 in FIGS. 1A and 1B (SEQ ID NO:2)) or as encoded by the cDNA clone contained in ATCC No. 97768 deposited on Oct. 22, 1996; (d) a nucleotide sequence encoding a polypeptide comprising the Neutrokine-α transmembrane domain (amino acid residues from about 47 to about 72 in FIGS. 1A and 1B (SEQ ID NO:2) or as encoded by the cDNA clone contained in ATCC No. 97768 deposited on Oct. 22, 1996; (e) a nucleotide sequence encoding a soluble Neutrokine a polypeptide having the extracellular and intracellular domains but lacking the transmembrane domain; and (f) a nucleotide sequence complementary to any of the nucleotide sequences in (a), (b), (c), (d) or (e) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e) or (f) above, or a polynucleotide which hybridizes under stringent hybridization conditions to a polynucleotide in (a), (b), (c), (d), (e) or (f) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a Neutrokine-α polypeptide having an amino acid sequence in (a), (b), (c), (d) or (e) above. A further nucleic acid embodiment of the invention relates to an isolated nucleic acid molecule comprising a polynucleotide which encodes the amino acid sequence of a Neutrokine-α polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polynucleotide which encodes the amino acid sequence of a Neutrokine-α polypeptide to have an amino acid sequence which contains not more than 10, 9, 8, 7, 6, 5, 4, 3, 2 or 1 amino acid substitutions. Conservative substitutions are preferable.

The present invention also relates to recombinant vectors, which include the isolated nucleic acid molecules of the present invention, and to host cells containing the recombinant vectors, as well as to methods of making such vectors and host cells and for using them for production of Neutrokine-α polypeptides or peptides by recombinant techniques.

The invention further provides an isolated Neutrokine-α polypeptide comprising an amino acid sequence selected from the group consisting of: (a) the amino acid sequence of the full-length Neutrokine-α polypeptide having the complete amino acid sequence shown in FIGS. 1A and 1B (SEQ ID NO:2) or as encoded by the cDNA clone contained in ATCC No. 97768 deposited on Oct. 22, 1996; (b) the amino acid sequence of the predicted extracellular domain of the Neutrokine-α polypeptide having the amino acid sequence at positions 73 to 285 in FIGS. 1A and 1B (SEQ ID NO:2) or as encoded by the cDNA clone contained in ATCC No. 97768 deposited on Oct. 22, 1996; (c) the amino acid sequence of the Neutrokine-α intracellular domain (amino acid residues from about 1 to about 46 in FIGS. 1A and 1B (SEQ ID NO:2)) or as encoded by the cDNA clone contained in ATCC No. 97768 deposited on Oct. 22, 1996; (d) the amino acid sequence of the Neutrokine-α transmembrane domain (amino acid residues from about 47 to about 72 in FIGS. 1A and 1B (SEQ ID NO:2)) or as encoded by the cDNA clone contained in ATCC No. 97768 deposited on Oct. 22, 1996; and (e) the amino acid sequence of the soluble Neutrokine-α polypeptide having the extracellular and intracellular domains but lacking the transmembrane domain, wherein each of these domains is defined above.

The polypeptides of the present invention also include polypeptides having an amino acid sequence with at least 90% similarity, and more preferably at least 95% similarity to those described in (a), (b), (c), (d) or (e) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope-bearing portion of a Neutrokine-α polypeptide having an amino acid sequence described in (a), (b), (c), (d) or (e) above. Peptides or polypeptides having the amino acid sequence of an epitope-bearing portion of a Neutrokine-α polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to an polypeptide having an amino acid sequence described in (a), (b), (c), (d) or (e) above.

The invention further provides methods for isolating antibodies that bind specifically to a Neutrokine-α polypeptide having an amino acid sequence as described herein. Such antibodies are useful diagnostically or therapeutically as described below.

The invention also provides for pharmaceutical compositions comprising soluble Neutrokine-α polypeptides, particularly human Neutrokine-α polypeptides, which may be employed, for instance, to treat tumor and tumor metastasis, infections by bacteria, viruses and other parasites, immunodeficiencies, inflammatory diseases, lymphadenopathy, autoimmune diseases, graft versus host disease and to stimulate peripheral tolerance, destroy some transformed cell lines, mediate cell activation and proliferation, and are functionally linked as primary mediators of immune regulation and inflammatory responses.

The invention further provides compositions comprising a Neutrokine-α polynucleotide or a Neutrokine-α polypeptide for administration to cells in vitro, to cells ex vivo and to cells in vivo, or to a multicellular organism. In certain particularly preferred embodiments of this aspect of the invention, the compositions comprise a Neutrokine-α polynucleotide for expression of a Neutrokine-α polypeptide in a host organism for treatment of disease. Particularly preferred in this regard is expression in a human patient for treatment of a dysfunction associated with aberrant endogenous activity of a Neutrokine-α gene.

The present invention also provides a screening method for identifying compounds capable of enhancing or inhibiting a cellular response induced by Neutrokine-α which involves contacting cells which express Neutrokine-α with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a method for identifying Neutrokine-α receptors is provided, as well as a screening assay for agonists and antagonists using such receptors. This assay involves determining the effect a candidate compound has on Neutrokine-α binding to the Neutrokine-α receptor. In particular, the method involves contacting a Neutrokine-α receptor with a Neutrokine-α polypeptide and a candidate compound and determining whether Neutrokine-α polypeptide binding to the Neutrokine-α receptor is increased or decreased due to the presence of the candidate compound. The antagonists may be employed to prevent septic shock, inflammation, cerebral malaria, activation of the HIV virus, graft-host rejection, bone resorption, rheumatoid arthritis and cachexia (wasting or malnutrition)

The present inventors have discovered that Neutrokine-α is expressed not only in neutrophils, but also in kidney, lung, peripheral leukocyte, bone marrow, T cell lymphoma, B cell lymphoma, activated T cells, stomach cancer, smooth muscle, macrophages, and cord blood tissue. For a number of disorders of these tissues and cells, such as tumor and tumor metastasis, infection of bacteria, viruses and other parasites, immunodeficiencies, septic shock, inflammation, cerebral malaria, activation of the HIV virus, graft-host rejection, bone resorption, rheumatoid arthritis and cachexia (wasting or malnutrition, it is believed that significantly higher or lower levels of Neutrokine-α gene expression can be detected in certain tissues (e.g., bone marrow) or bodily fluids (e.g., serum, plasma, urine, synovial fluid or spinal fluid) taken from an individual having such a disorder, relative to a "standard" Neutrokine-α gene expression level, i.e., the Neutrokine-α expression level in tissue or bodily fluids from an individual not having the disorder. Thus, the invention provides a diagnostic method useful during diagnosis of a disorder, which involves: (a) assaying Neutrokine-α gene expression level in cells or body fluid of an individual; (b) comparing the Neutrokine-α gene expression level with a standard Neutrokine-α gene expression level, whereby an increase or decrease in the assayed Neutrokine-α gene expression level compared to the standard expression level is indicative of a disorder.

An additional aspect of the invention is related to a method for treating an individual in need of an increased level of Neutrokine-α activity in the body comprising administering to such an individual a composition comprising a therapeutically effective amount of an isolated Neutrokine-α polypeptide of the invention or an agonist thereof.

A still further aspect of the invention is related to a method for treating an individual in need of a decreased level of Neutrokine-α activity in the body comprising, administering to such an individual a composition comprising a therapeutically effective amount of an Neutrokine-α antagonist. Preferred antagonists for use in the present invention are Neutrokine-α-specific antibodies.

BRIEF DESCRIPTION OF THE FIGURES

FIGS. 1A and 1B show the nucleotide (SEQ ID NO:1) and deduced amino acid (SEQ ID NO:2) sequences of the Neutrokine-α protein. Amino acids 1 to 46 represent the intracellular domain, amino acids 47 to 72 the transmembrane domain (the underlined sequence), and amino acids 73 to 285, the extracellular domain (the remaining sequence).

FIGS. 2A–C show the regions of identity between the amino acid sequences of the Neutrokine-α protein (SEQ ID NO:2) and TNF-α (SEQ ID NO:3), TNF-β (lymphotoxin; SEQ ID NO:4), LT beta (SEQ ID NO:5) and FAS ligand (SEQ ID NO:6), determined by the "Megalign" routine which is part of the computer program called "DNAStar". Amino acid residues that match the consensus are shaded.

FIGS. 4A–C show the alignment of the Neutrokine-α nucleotide sequence HDNEDU15; (SEQ ID NO:1) determined from the human cDNA deposited in ATCC No. 97768 deposited on Oct. 22, 1996 with related human cDNA clones of the invention which have been designated HSOAD55 (SEQ ID NO:7), HSLAH84 (SEQ ID NO:8) and HLTBM08 (SEQ ID NO:9).

DETAILED DESCRIPTION

Figure 3:
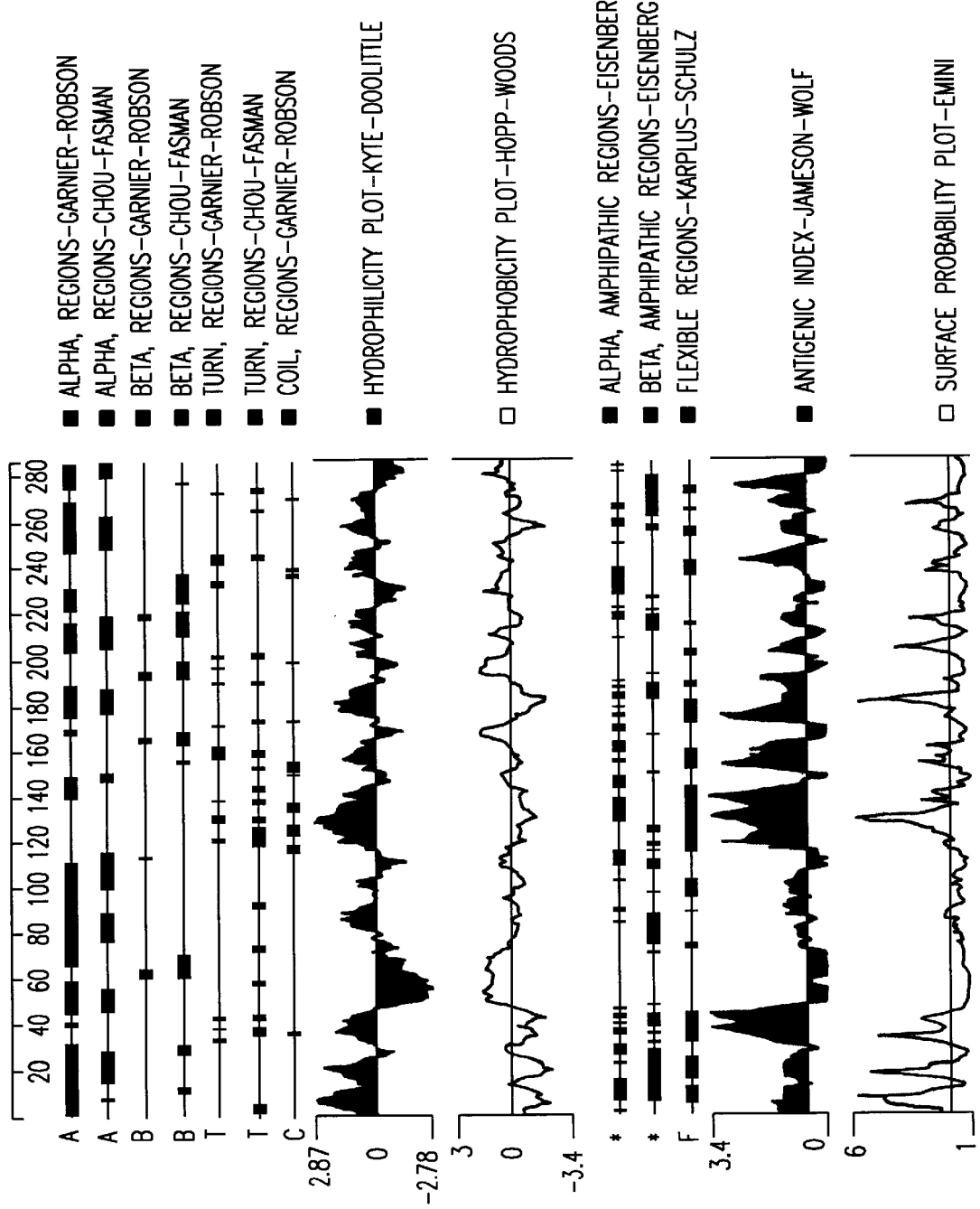
FIG. 3 shows an analysis of the Neutrokine-α amino acid sequence (SEQ ID NO:2). Alpha, beta, turn and coil regions; hydrophilicity and hydrophobicity; amphipathic regions; flexible regions; antigenic index and surface probability are shown. In the "Antigenic Index—Jameson-Wolf" graph, the indicate location of the highly antigenic regions of the Neutrokine-α protein, i.e., regions from which epitope-bearing peptides of the invention may be obtained.

The present invention provides isolated nucleic acid molecules comprising a polynucleotide encoding Neutrokine-α polypeptide having the amino acid sequence shown in FIGS. 1A and 1B (SEQ ID NO:2), which was determined by sequencing a cloned cDNA Neutrokine-α. The nucleotide sequence shown in FIGS. 1A and 1B (SEQ ID NO:1) was obtained by sequencing the HNEDU15 clone, which was deposited on Oct. 22, 1996 at the American Type Culture Collection, 10801 University Drive, Manassas, Va. 20110-2209 and assigned ATCC Deposit No. 97768. The deposited clone is contained in the pBluescript SK(-) plasmid (Stratagene, La Jolla, Calif.).

Figure 2A:
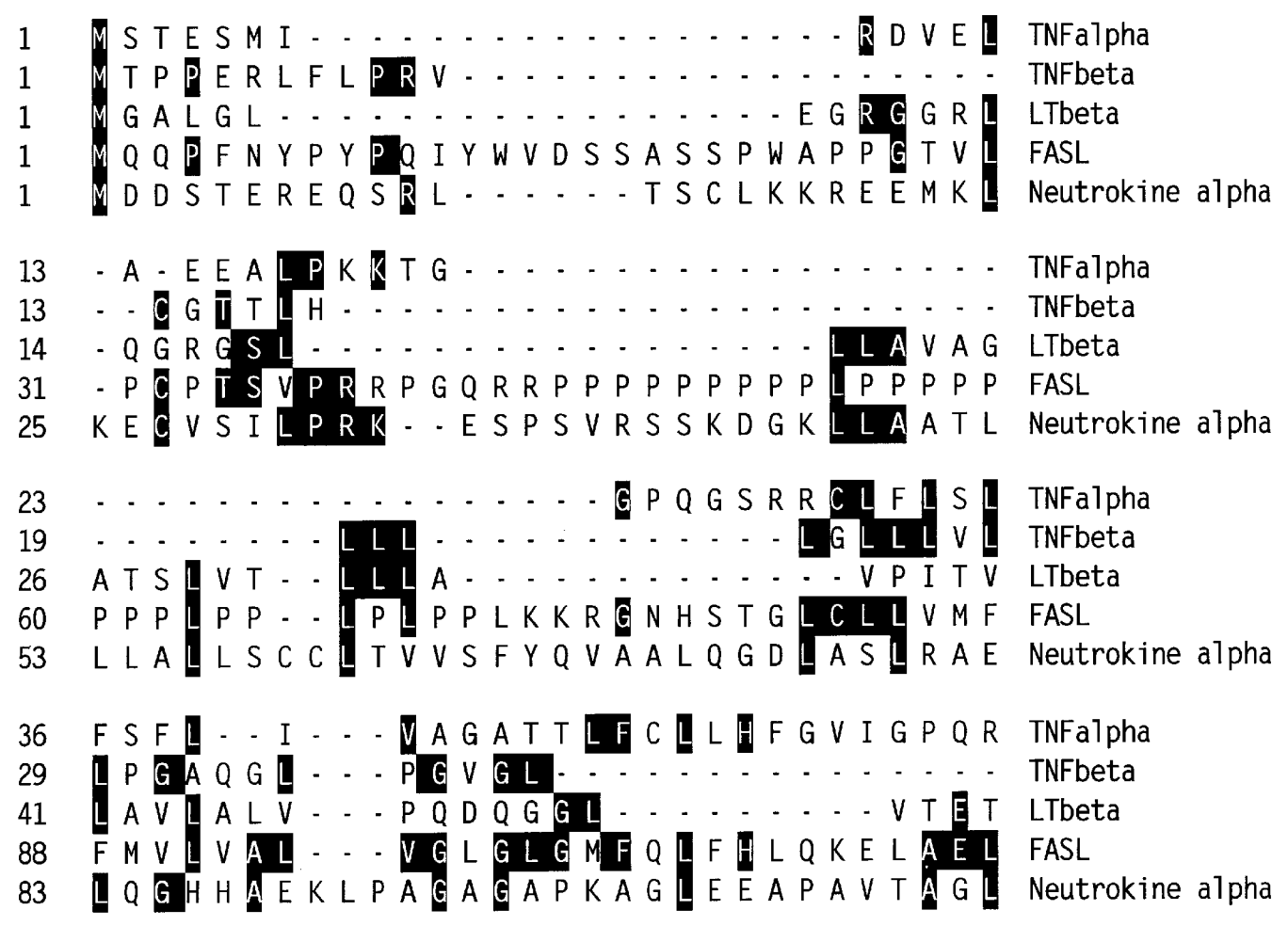
Figure 2B:
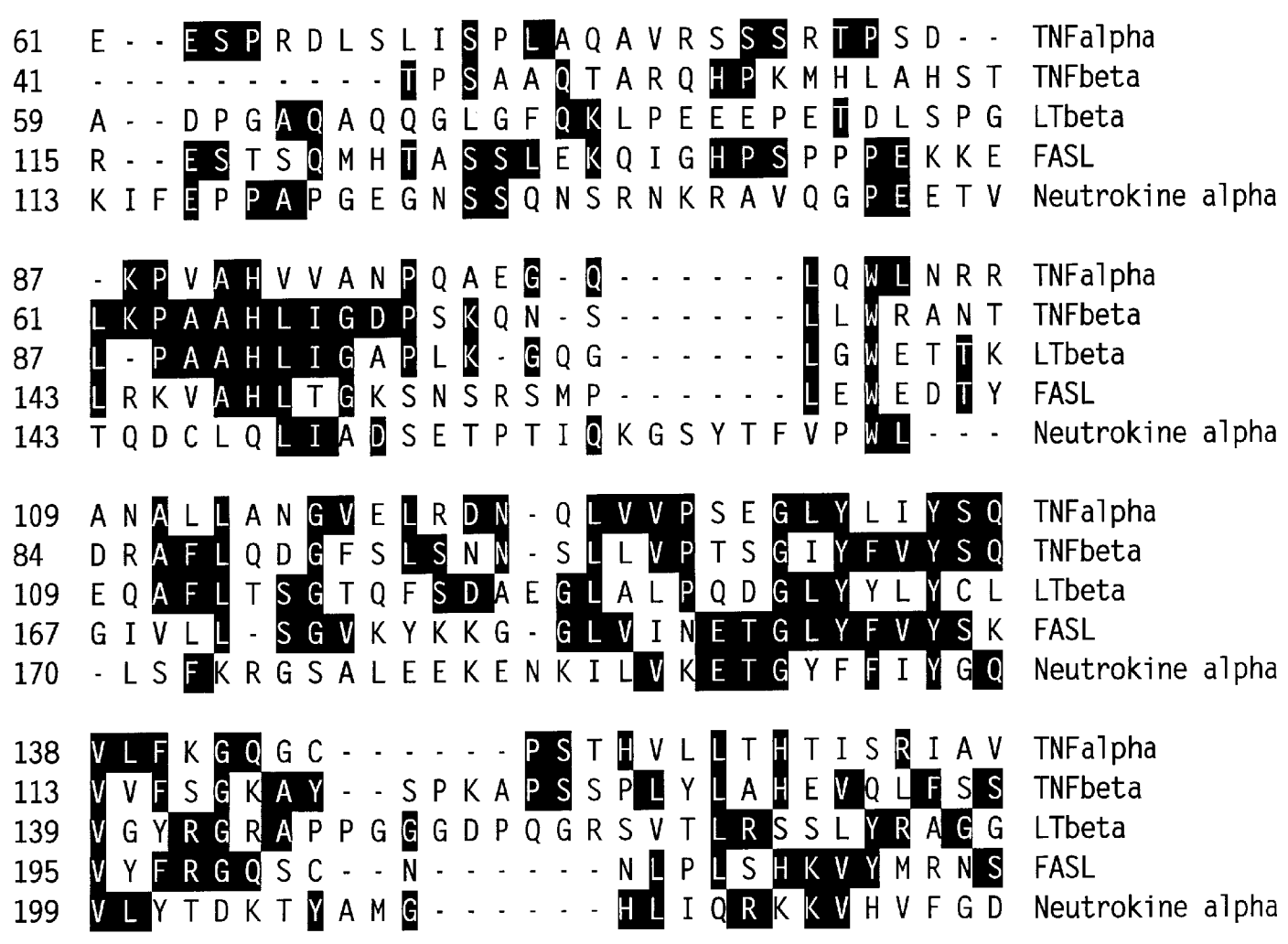

The Neutrokine-α protein of the present invention shares sequence homology with the translation product of the human mRNAs for TNF-α, TNF-β and Fas ligand (FIGS. 2A–C). As noted above, TNF-α is thought to be an important cytokine that plays a role in cytotoxicity, necrosis, apoptosis, costimulation, proliferation, lymph node formation, immunoglobulin class switch, differentiation, antiviral activity, regulation of adhesion molecules and other cytokines and growth factors.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A and 1B, a nucleic acid molecule of the present invention encoding a Neutrokine-α polypeptide may be obtained using standard cloning and screening procedures, such as those for cloning cDNAs using mRNA as starting material. Illustrative of the invention, the nucleic acid molecule described in FIGS. 1A and 1B (SEQ ID NO:1) was discovered in a cDNA library derived from neutrophils. Expressed sequence tags corresponding to a portion of the Neutrokine-α cDNA were also found in kidney, lung, peripheral leukocyte, bone marrow, T cell lymphoma, B cell lymphoma, activated T cells, stomach cancer, smooth muscle, macrophages, and cord blood tissue.

The Neutrokine-α gene contains an open reading frame encoding a protein of about 285 amino acid residues, an intracellular domain of about 46 amino acids (amino acid residues from about 1 to about 46 in FIGS. 1A and 1B (SEQ ID NO:2)), a transmembrane domain of about 26 amino acids (underlined amino acid residues from about 47 to about 72 in FIGS. 1A and 1B (SEQ ID NO2)), an extracellular domain of about 213 amino acids (amino acid residues from about 73 to about 285 in FIGS. 1A and 1B (SEQ ID NO:2)); and a deduced molecular weight of about 31 kDa. The Neutrokine-α protein shown in FIGS. 1A and 1B (SEQ ID NO: 2) is about 20% similar and about 10% identical to human TNF-α which can be accessed on GenBank as Accession No. 339764.

As one of ordinary skill would appreciate, due to the possibilities of sequencing errors discussed above, the actual complete Neutrokine-α polypeptide encoded by the deposited cDNA, which comprises about 285 amino acids, may be somewhat shorter. In particular, the determined Neutrokine-α coding sequence contains a second methionine codon which may serve as an alternative start codon for translation of the open reading frame, at nucleotide positions 210–213 in FIGS. 1A and 1B (SEQ ID NO:1). More generally, the actual open reading frame may be anywhere in the range of ±20 amino acids, more likely in the range of ±10 amino acids, of that predicted from either the first or second methionine codon from the N-terminus shown in FIG. 1 (SEQ ID NO:1). It will further be appreciated that, depending on the analytical criteria used for identifying various functional domains, the exact "address" of the extracelluar, intracelluar and transmembrane domains of the Neutrokine-α polypeptide may differ slightly. For example, the exact location of the Neutrokine-α extracellular domain in FIGS. 1A and 1B (SEQ ID NO:2) may vary slightly (e.g., the address may "shift" by about 1 to about 20 residues, more likely about 1 to about 5 residues) depending on the criteria used to define the domain. In this case, the ends of the transmembrane domain and the beginning of the extracellular domain were predicted on the basis of the identification of the hydrophobic amino acid sequence in the above indicated positions, as shown in FIG. 3. In any event, as discussed further below, the invention further provides polypeptides having various residues deleted from the N-terminus of the complete polypeptide, including polypeptides lacking one or more amino acids from the N-terminus of the extracellular domain described herein, which constitute soluble forms of the extracellular domain of the Neutrokine-α protein.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 147–149 of the nucleotide sequence shown in FIGS. 1A and 1B (SEQ ID NO:1). In addition, isolated nucleic acid molecules of the invention include DNA molecules which comprise a sequence substantially different from those described above but which, due to the degeneracy of the genetic code, still encode the Neutrokine-α protein. Of course, the genetic code is well known in the art. Thus, it would be routine for one skilled in the art to generate the degenerate variants described above. In another aspect, the invention provides isolated nucleic acid molecules encoding the Neutrokine-α polypeptide having an amino acid sequence encoded by the cDNA contained in the plasmid deposited on Oct. 22, 1996. Preferably, this nucleic acid molecule will comprise a sequence encoding the extracellular domain of the polypeptide encoded by the above-described deposited cDNA clone.

The invention further provides an isolated nucleic acid molecule having the nucleotide sequence shown in FIGS. 1A and 1B (SEQ ID NO:1) or the nucleotide sequence of the Neutrokine-α cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the Neutrokine-α gene in human tissue, for instance, by Northern blot analysis.

The invention also provides nucleic acid molecules having nucleotide sequences related to extensive portions of SEQ ID NO:1 which have been determined from the following related cDNA clones: HSOAD55 (SEQ ID NO:7), HSLAH84 (SEQ ID NO:8), and HLTBM08 (SEQ ID NO:9).

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 147–1001 of SEQ ID NO:1.

Further, the invention includes a polynucleotide comprising a sequence at least 95% identical to any portion of at least about 30 contiguous nucleotides, preferably at least about 50 nucleotides, of the sequence from nucleotide 1 to nucleotide 1082 in FIGS. 1A and 1B (SEQ ID NO:1), preferably excluding the nucleotide sequences determined from the abovelisted cDNA clones and the nucleotide sequences from nucleotide 797 to 1082, 810 to 1082, and 346 to 542. More preferably, the invention includes a polynucleotide comprising nucleotide residues 147–500, 147–450, 147–400, 147, 350, 200–500, 200–450, 200–400, 200–350, 250–500, 250–450, 250–400, 250–350, 300–500, 300–450, 300–400, 300–350, 350–750, 350–700, 350–650, 350–600, 350–550, 400–750, 400–700, 400–650, 400–600, 400–550, 425–750, 425–700, 425–650, 425–600, 425–550, 450–1020, 450–1001, 450–950, 450–900, 450–850, 450–800, 450–775, 500–1001, 500–950, 500–900, 500–850, 500–800, 500–775, 550–1001, 550–950, 550–900, 550–850, 550–800, 550–775, 600–1001, 600–950, 600–900, 600–850, 600–800, 600–775, 650–1001, 650–950, 650–900, 650–850, 650–800, 650–775, 700–1001, 700–950, 700–900, 700–850, 700–800, 700–775, 825–1082, 850–1082, 875–1082, 900–1082, 925–1082, 950–1082, 975–1082, 1000–1082, 1025–1082, and 1050–1082.

More generally, by a fragment of an isolated nucleic acid molecule having the nucleotide sequence of the deposited cDNA or the nucleotide sequence shown in FIGS. 1A and 1B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A and 1B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A and 1B (SEQ ID NO:1). Preferred nucleic acid fragments of the present invention include nucleic acid molecules encoding epitope-bearing portions of the Neutrokine-α polypeptide as identified in FIGS. 1A and 1B and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC No. 97768 deposited on Oct. 22, 1996. By "stringent hybridization conditions" is intended overnight incubation at 42° C. in a solution comprising: 50% formamide, 5× SSC 750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A and 1B (SEQ ID NO:1)). Of course, a polynucleotide which hybridizes only to a poly A sequence (such as the 3' terminal poly(A) tract of the Neutrokine-α cDNA shown in FIGS. 1A and 1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a Neutrokine-α polypeptide may include, but are not limited to those encoding the amino acid sequence of the extracellular domain of the polypeptide, by itself; and the coding sequence for the extracellular domain of the polypeptide and additional sequences, such as those encoding the intracellular and transmembrane domain sequences, or a pre-, or pro- or prepro- protein sequence; the coding sequence of the extracellular domain of the polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the Neutrokine-α fused to Fc at the N- or C-terminus.

Variant and Mutant Polynucleotides

The present invention further relates to variants of the nucleic acid molecules of the present invention, which encode portions, analogs or derivatives of the Neutrokine-α protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Neutrokine-α protein or portions thereof. Also especially preferred in this regard are conservative substitutions.

Most highly preferred are nucleic acid molecules encoding the extracellular domain of the protein having the amino acid sequence shown in FIGS. 1A and 1B (SEQ ID NO:2) or the extracellular domain of the Neutrokine-α amino acid sequence encoded by the deposited cDNA clone. Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding the Neutrokine-α polypeptide having the complete amino acid sequence in FIGS. 1A and 1B (SEQ ID NO:2); (b) a nucleotide sequence encoding the predicted extracellular domain of the Neutrokine-α polypeptide having the amino acid sequence at positions 73–285 in FIGS. 1A and 1B (SEQ ID NO:2); (c) a nucleotide sequence encoding the Neutrokine-α polypeptide having the complete amino acid sequence encoded by the cDNA clone contained in ATCC No. 97768 deposited on Oct. 22, 1996; (d) a nucleotide sequence encoding the extracellular domain of the Neutrokine-α polypeptide having the amino acid sequence encoded by the cDNA clone contained in ATCC No. 97768 deposited on Oct. 22, 1996; and (e) a nucleotide sequence complementary to any of the nucleotide sequences in (a), (b), (c) or (d) above.

By a polynucleotide having a nucleotide sequence at least, for example, 95% "identical" to a reference nucleotide sequence encoding a Neutrokine-α polypeptide is intended that the nucleotide sequence of the polynucleotide is identical to the reference sequence except that the polynucleotide sequence may include up to five point mutations per each 100 nucleotides of the reference nucleotide sequence encoding the Neutrokine-α polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A and 1B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIGS. 1A and 1B (SEQ ID NO:1) or to the nucleic acid sequence of the deposited cDNA, irrespective of whether they encode a polypeptide having Neutrokine-α activity. This is because even where a particular nucleic acid molecule does not encode a polypeptide having Neutrokine-α activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Neutrokine-α activity include, inter alia, (1) isolating the Neutrokine-α gene or allelic variants thereof in a cDNA library; (2) in situ hybridization (e.g., "FISH") to metaphase chromosomal spreads to provide precise chromosomal location of the Neutrokine-α gene, as described in Verma et al., *Human Chromosomes: A Manual of Basic Techniques*, Pergamon Press, New York (1988); and Northern Blot analysis for detecting Neutrokine-α mRNA expression in specific tissues.

Preferred, however, are nucleic acid molecules having sequences at least 90%, 95%, 96%, 97%, 98% or 99% identical to the nucleic acid sequence shown in FIGS. 1A and 1B (SEQ ID NO:1) or to the nucleic acid sequence of the deposited cDNA which do, in fact, encode a polypeptide having Neutrokine-α protein activity. By "a polypeptide having Neutrokine-(α activity" is intended polypeptides exhibiting activity similar, but not necessarily identical, to an activity of the extracellular domain or of the full-length Neutrokine-α protein of the invention, as measured in a particular biological assay. For example, the Neutrokine-α protein of the present invention modulates cell proliferation, cytotoxicity and cell death. An in vitro cell proliferation, cytotoxicity and cell death assay for measuring the effect of a protein on certain cells can be performed by using reagents well known and commonly available in the art for detecting cell replication and/or death. For instance, numerous such assays for TNF-related protein activities are described in the various references in the Background section of this disclosure, above. Briefly, such an assay involves collecting human or animal (e.g., mouse) cells and mixing with (1) transfected host cell-supernatant containing Neutrokine-α protein (or a candidate polypeptide) or (2) nontransfected host cell-supernatant control, and measuring the effect on cell numbers or viability after incubation of certain period of time. Such cell proliferation modulation activities as can be measure in this type of assay are useful for treating tumor, tumor metastasis, infections, autoimmune diseases inflammation and other immune-related diseases.

Neutrokine-α modulates cell proliferation and differentiation in a dose-dependent manner in the above-described assay. Thus, "a polypeptide having Neutrokine α protein activity" includes polypeptides that also exhibit any of the same cell modulatory (particularly immunomodulatory) activities in the above-described assays in a dose-dependent manner. Although the degree of dose-dependent activity need not be identical to that of the Neutrokine-α protein, preferably, "a polypeptide having Neutrokine-α protein activity" will exhibit substantially similar dose-dependence in a given activity as compared to the Neutrokine-α protein (i.e., the candidate polypeptide will exhibit greater activity or not more than about 25-fold less and, preferably, not more than about tenfold less activity relative to the reference Neutrokine-α protein).

Like other members of TNF family, Neutrokine-α exhibits activity on leukocytes including for example monocytes, lymphocytes and neutrophils. For this reason Neutrokine-α is active in directing the proliferation, differentiation and migration of these cell types. Such activity is useful for immune enhancement or suppression, myeloprotection, stem cell mobilization, acute and chronic inflammatory control and treatment of leukemia. Assays for measuring such activity are known in the art. For example, see Peters et al., *Immun. Today* 17:273 (1996); Young et al., *J. Exp. Med.* 182:1111 (1995); Caux et al., *Nature* 390:258 (1992); and Santiago-Schwarz et al., *Adv. Exp. Med. Biol.* 378:7 (1995)."

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having Neutrokine-α protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Neutrokine-α protein activity. This is because the skilled artisan is fully aware of amino acid substitutions that are either less likely or not likely to significantly effect protein function (e.g., replacing one aliphatic amino acid with a second aliphatic amino acid), as further described below. A further nucleic acid embodiment of the invention relates to an isolated nucleic acid molecule comprising a polynucleotide which encodes the amino acid sequence of a Neutrokine-α polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a polynucleotide which encodes the amino acid sequence of a Neutrokine-α polypeptide to have an amino acid sequence which contains not more than 10, 9, 8, 7, 6, 5, 4, 3, 2 or 1 conservative amino acid substitutions.

Vectors and Host Cells

The present invention also relates to vectors which include the isolated DNA molecules of the present invention, host cells which are genetically engineered with the recombinant vectors, and the production of Neutrokine-α polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells. The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the extracellular domain of the transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pHE4-5 (ATCC Accession No. 209311; and variations thereof), pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The polypeptide may be expressed in a modified form, such as a fusion protein, and may include not only secretion signals, but also additional. heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5 has been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

The Neutrokine-α protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Neutrokine-α Polypeptides and Fragments

The invention further provides an isolated Neutrokine-α polypeptide having the amino acid sequence encoded by the deposited cDNA, or the amino acid sequence in FIGS. 1A and 1B (SEQ ID NO:2), or a peptide or polypeptide comprising a portion of the above polypeptides.

Variant and Mutant Polypeptides

To improve or alter the characteristics of Neutrokine-α polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing.

In the present case, since the protein of the invention is a member of the TNF polypeptide family, deletions of N-terminal amino acids up to the Gly (G) residue at position 191 in FIGS. 1A and 1B (SEQ ID NO:2) may retain some biological activity such as cytotoxicity to appropriate target cells. Polypeptides having further N-terminal deletions including the Gly (G) residue would not be expected to retain such biological activities because it is known that this residue in TNF-related polypeptides is in the beginning of the conserved domain required for biological activities. However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or extracellular domain of the protein generally will be retained when less than the majority of the residues of the complete or extracellular domain of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues from the amino terminus of the amino acid sequence of the Neutrokine-α shown in FIG. 1 (SEQ ID NO:2), up to the glycine residu at position 191 (Gly-191 residue from the amino terminus), and polynucleotides encoding such polypeptides. In particular, the present invention provides polypeptides having the amino acid sequence of residues n- 285 of SEQ ID NO:2, where n is an integer in the range of 2–190 and 191 is the position of the first residue from the N-terminus of the complete Neutrokine-α polypeptide (shown in SEQ ID NO:2) believed to be required for activity of the Neutrokine-α protein. More in particular, the invention provides polynucleotides encoding polypeptides having the amino acid sequence of residues 2–285, 3–285, 4–285, 5–285, 6–285, 7–285, 8–285, 9–285, 10–285, 11–285, 12–285, 13–285, 14–285, 15–258, 16–285, 17–285, 18–285, 19–285, 20–285, 21–285, 22–285, 23–285, 24–285, 25–285, 26–285, 27–285, 28–285, 29–285, 30–285, 31–285, 32–285, 33–285, 34–285, 35–285, 36–285, 37–285, 38–285, 39–285, 40–285, 41–285, 42–285, 43–285, 44–285, 45–285, 46–285, 47–285, 48–285, 49–285, 50–285, 51–285, 52–285, 53–285, 54–285, 55–285, 56–285, 57–285, 58–285, 59–285, 60–285, 61–285, 62–285, 63–285, 64–285, 65–285, 66–285, 67–285, 68–285, 69–285, 70–285, 71–285, 72–285, 73–285, 74–285, 75–285, 76–285, 77–285, 78–285, 79–285, 80–285, 81–285, 82–285, 83–285, 84–285, 85–285, 86–285, 87–285, 88–285, 89–285, 90–285, 91–285, 92–285, 93–285, 94–285, 95–285, 96–285, 97–285, 98–285, 99–285, 100–285, 101–285, 102–285, 103–285, 104–285, 105–285, 106–285, 107–285, 108–285, 109–285, 110–285, 111–285, 112–285, 113–285, 114–285, 115–285, 116–285, 117–285, 118–285, 119–285, 120–285, 121–285, 122–285, 123–285, 124–285, 125–285, 126–285, 127–285, 128–285, 129–285, 130–285, 131–285, 132–285, 133–285, 134–285, 135–285, 136–285, 137–285, 138–285, 139–285, 140–285, 141–285, 142–285, 143–285, 144–285, 145–285, 146–285, 147–285, 148–285, 149–285, 150–285, 151–285, 152–285, 153–285, 154–285, 155–285, 156–285, 157–285, 158–285, 159–285, 160–285, 161–285, 162–285, 163–285, 164–285, 165–285, 166–285, 167–285, 168–285, 169–285, 170–285, 171–285, 172–285, 173–285, 174–285, 175–285, 176–285, 177–285, 178–285, 179–285, 180–285, 181–285, 182–285, 183–285, 184–285, 185–285, 186–285, 187–285, 188–285, 189–285, and 190–285 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Döbeli et al., *J. Biotechnology* 7:199–216 (1988). Since the present protein is a member of the TNF polypeptide family, deletions of C-terminal amino acids up to the leucine residue at position 284 are expected to retain most if not all biological activity such as receptor binding and modulation of cell replication. Polypeptides having deletions of up to about 10 additional C-terminal residues (i.e., up to the glycine residue at position 273) also may retain some activity such as receptor binding, although such polypeptides would lack a portion of the conserved TNF domain beginning at about Leu-284. However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the Neutrokine-α shown in FIGS. 1A and 1B (SEQ ID NO:2), up to the glycine residue at position 274 (Gly-274) and polynucleotides encoding such polypeptides. In particular, the present invention provides polypeptides having the amino acid sequence of residues 1-m of the amino acid sequence in SEQ ID NO:2, where m is any integer in the range of 274 to 284. More in particular, the invention provides polynucleotides encoding polypeptides having the amino acid sequence of residues 1–274, 1–275, 1–276, 1–277, 1–278, 1–279, 1–280, 1–281, 1–282, 1–283 and 1–284 of SEQ ID NO:2. Polynucleotides encoding these polypeptides also are provided.

Also provided are polypeptides having one or more amino acids deleted from both the amino and the carboxyl termini, which may be described generally as having residues n-m of SEQ ID NO:2, where n and m are integers as described above. Also included are a nucleotide sequence encoding a polypeptide consisting of a portion of the complete Neutrokine-α amino acid sequence encoded by the cDNA clone contained in ATCC No. 97768 deposited on Oct. 22, 1996 where this portion excludes from 1 to 190 amino acids from the amino terminus or from 1 to 11 amino acids from the C-terminus of the complete amino acid sequence (or any combination of these N-terminal and C-terminal deletions) encoded by the cDNA clone in the deposited clone. Polynucleotides encoding all of the above deletion polypeptides also are provided.

Other Mutants

In addition to terminal deletion forms of the protein discussed above, it will be recognized by one of ordinary skill in the art that some amino acid sequences of the Neutrokine-α polypeptide can be varied without significant effect of the structure or function of the protein. If such differences in sequence are contemplated, it should be remembered that there will be critical areas on the protein which determine activity.

Thus, the invention further includes variations of the Neutrokine-α polypeptide which show substantial Neutrokine-α polypeptide activity or which include regions of Neutrokine-α protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of FIGS. 1A and 1B (SEQ ID NO:2), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the extracellular domain of the polypeptide is fused with another compound, such as a compound to increase the half-life of the polypeptide (for example, polyethylene glycol), or (iv) one in which the additional amino acids are fused to the extracellular domain of the polypeptide, such as an IgG Fc fusion region peptide or leader or secretory sequence or a sequence which is employed for purification of the extracellular domain of the polypeptide or a proprotein sequence. Such fragments, derivatives and analogs are deemed to be within the scope of those skilled in the art from the teachings herein.

Thus, the Neutrokine-α of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the Neutrokine-α protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., *Diabetes* 36: 838–845 (1987); Cleland et al., *Crit. Rev. Therapeutic Drug Carrier Systems* 10:307–377 (1993).

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Since Neutrokine-α is a member of the TNF polypeptide family, mutations similar to those in TNF-α are likely to have similar effects in Neutrokine-α.

Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)). Since Neutrokine-α is a member of the TNF-related protein family, to modulate rather than completely eliminate biological activities of Neutrokine-α, preferably mutations are made in sequences encoding amino acids in the TNF conserved domain, i.e., in positions 191–284 of FIGS. 1A and 1B (SEQ ID NO:2), more preferably in residues within this region which are not conserved in all members of the TGF family.

By making a specific mutation in Neutrokine-α in the position where such a conserved amino acid is typically found in related TNFs, Neutrokine-α will act as an antagonist, thus possessing angiogenic activity. Accordingly, polypeptides of the present invention include Neutrokine-α mutants. Such Neutrokine-α mutants are comprised of the full-length or preferably the extracellular domain of the Neutrokine-α amino acid sequence shown in FIGS. 1A and 1B (SEQ ID NO:2). Also forming part of the present invention are isolated polynucleotides comprising nucleic acid sequences which encode the above Neutrokine-α mutants.

The polypeptides of the present invention are preferably provided in an isolated form, and preferably are substantially purified. A recombinantly produced version of the Neutrokine-α polypeptide can be substantially purified by the one-step method described in Smith and Johnson, *Gene* 67:31–40 (1988).

The polypeptides of the present invention include the complete polypeptide encoded by the deposited cDNA including the intracellular, transmembrane and extracellular domains of the polypeptide encoded by the deposited cDNA, the extracellular domain minus the intracellular and transmembrane domains of the protein, the complete polypeptide of FIGS. 1A and 1B (SEQ ID NO:2), the extracellular domain of FIGS. 1A and 1B (SEQ ID NO:2) minus the intracellular and transmembrane domains, as well as polypeptides which have at least 90% similarity, more preferably at least 95% similarity, and still more preferably at least 96%, 97%, 98% or 99% similarity to those described above.

Further polypeptides of the present invention include polypeptides at least 80% identical, more preferably at least 90% or 95% identical, still more preferably at least 96%, 97%, 98% or 99% identical to the Polypeptide encoded by the deposited cDNA or to the polypeptide of FIGS. 1A and 1B (SEQ ID NO:2), and also include portions of such polypeptides with at least 30 amino acids and more preferably at least 50 amino acids.

A further embodiment of the invention relates to a peptide or polypeptide which comprises the amino acid sequence of a Neutrokine-α polypeptide having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions. Of course, in order of ever-increasing preference, it is highly preferable for a peptide or polypeptide to have an amino acid sequence which comprises the amino acid sequence of a Neutrokine-α polypeptide, which contains at least one, but not more than 10, 9, 8, 7, 6, 5, 4, 3, 2 or 1 conservative amino acid substitutions.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a Neutrokine-α polypeptide is intended that the amino acid sequence of the polypeptide is identical to the reference sequence except that the polypeptide sequence may include up to five amino acid alterations per each 100 amino acids of the reference amino acid of the Neutrokine-α polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and 1B (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Neutrokine-α protein expression as described below or as agonists and antagonists capable of enhancing or inhibiting Neutrokine-α protein function. Further, such polypeptides can be used in the yeast two-hybrid system to "capture" Neutrokine-α protein binding proteins which are also candidate agonists and antagonists according to the present invention. The yeast two hybrid system is described in Fields and Song, Nature 340:245–246 (1989).

Epitope-bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins", Science, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., Cell 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate Neutrokine-α specific antibodies include: a polypeptide comprising, amino acid residues from about Phe-115 to about Leu-147 in FIGS. 1A and 1B (SEQ ID NO:2); a polypeptide comprising, amino acid residues from about Il-150 to about Tyr-163 in FIGS. 1A and 1B (SEQ ID NO:2); a polypeptide comprising amino acid residues from about Ser-171 to about Phe-194 in FIGS. 1A and 1B ((SEQ ID NO:2); a polypeptide comprising amino acid residues from about Glu-223 to about Tyr-247 in FIGS. 1A and 1B (SEQ ID NO:2); a polypeptide comprising amino acid residues from about Ser-271 to about Phe-278 in FIGS. 1A and 1B (SEQ ID NO:2); These polypeptide fragments have been determined to bear antigenic epitopes of the Neutrokine-α protein by the analysis of the Jameson-Wolf antigenic index, as shown in FIG. 3, above.

The epitope-bearing peptides and polypeptides of the invention may be produced by any conventional means. See, e.g., Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, Neutrokine-α polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric Neutrokine-α protein or protein fragment alone (Fountoulakis et al., J. Biochem. 270:3958–3964 (1995)).

Immune System-related Disorder Diagnosis

The present inventors have discovered that Neutrokine-α is expressed in various tissues and particularly in neutrophils. For a number of immune system-related disorders, substantially altered (increased or decreased) levels of Neutrokine-α gene expression can be detected in immune system tissue or other cells or bodily fluids (e.g., sera, plasma, urine, synovial fluid or spinal fluid) taken from an individual having such a disorder, relative to a "standard" Neutrokine-α gene expression level, that is, the Neutrokine-α expression level in immune system tissues or bodily fluids from an individual not having the immune system disorder. Thus, the invention provides a diagnostic method useful during diagnosis of an system disorder, which involves measuring the expression level of the gene encoding the Neutrokine-α protein in immune system tissue or other cells or body fluid from an individual and comparing the measured gene expression level with a standard Neutrokine-α gene expression level, whereby an increase or decrease in the gene expression level compared to the standard is indicative of an immune system disorder.

In particular, it is believed that certain tissues in mammals with cancer of the immune express significantly enhanced or reduced levels of the Neutrokine-α protein and mRNA encoding the Neutrokine-α protein when compared to a corresponding "standard" level. Further, it is believed that enhanced or depressed levels of the Neutrokine-α protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a immune system disorder, including cancers of this system, which involves measuring the expression level of the gene encoding the Neutrokine-α protein in immune system tissue or other cells or body fluid from an individual and comparing the measured gene expression level with a standard Neutrokine-α gene expression level, whereby an increase or decrease in the gene expression level compared to the standard is indicative of an immune system disorder.

Where a diagnosis of a disorder in the immune system, including diagnosis of a tumor, has already been made according to conventional methods, the present invention is useful as a prognostic indicator, whereby patients exhibiting enhanced or depressed Neutrokine-α gene expression will experience a worse clinical outcome relative to patients expressing the gene at a level nearer the standard level.

By "assaying the expression level of the gene encoding the Neutrokine-α protein" is intended qualitatively or quantitatively measuring or estimating the level of the Neutrokine-α protein or the level of the mRNA encoding the Neutrokine-α protein in a first biological sample either directly (e.g., by determining or estimating absolute protein level or mRNA level) or relatively (e.g., by comparing to the Neutrokine-α protein level or mRNA level in a second biological sample). Preferably, the Neutrokine-α protein level or mRNA level in the first biological sample is measured or estimated and compared to a standard Neutrokine-α protein level or mRNA level, the standard being taken from a second biological sample obtained from an individual not having the disorder or being determined by averaging levels from a population of individuals not having a disorder of the immune system. As will be appreciated in the art, once a standard Neutrokine-α protein level or mRNA level is known, it can be used repeatedly as a standard for comparison.

By "biological sample" is intended any biological sample obtained from an individual, body fluid, cell line, tissue culture, or other source which contains Neutrokine-α protein or mRNA. As indicated, biological samples include body fluids (such as sera, plasma, urine, synovial fluid and spinal fluid) which contain free extracellular domains of the Neutrokine-α protein, immune system tissue, and other tissue sources found to express complete or free extracellular domain of the Neutrokine-α or a Neutrokine-α receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include but are not limited to tumors and tumor metastasis, infections by bacteria, viruses and other parasites, immunodeficiencies, inflammatory diseases, lymphadenopathy, autoimmune diseases, and graft versus host disease.

Total cellular RNA can be isolated from a biological sample using any suitable technique such as the single-step guanidinium-thiocyanate-phenol-chloroform method described in Chomczynski and Sacchi, Anal. Biochem. 162:156–159 (1987). Levels of mRNA encoding the Neutrokine-α protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying Neutrokine-α protein levels in a biological sample can occur using antibody-based techniques. For example, Neutrokine-α protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting Neutrokine α protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying Neutrokine-α protein levels in a biological sample obtained from an individual, Neutrokine-α protein can also be detected in vivo by imaging. Antibody labels or markers for in vivo imaging of Neutrokine-α protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A Neutrokine-α protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a in zradioisotope moiety, for a human subject, the quantity of radioactivity injected will normally range from about 5 to 20 millicuries of $^{99m}$Tc. The labeled antibody or antibody fragment will then preferentially accumulate at the location of cells which contain Neutrokine-α protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Antibodies

Neutrokine-α-protein specific antibodies for use in the present invention can be raised against the intact Neutrokine-α protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to Neutrokine-α protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the Neutrokine-α protein or an antigenic fragment thereof can be administered to an animal in order to induce the production of sera containing polyclonal antibodies. In a preferred method, a preparation of Neutrokine-α protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or Neutrokine-α protein binding fragments thereof). Such monoclonal antibodies can be prepared using hybridoma technology (Köhler et al., *Nature* 256:495 (1975); Köhler et al., *Eur. J. Immunol.* 6:511 (1976); Köhler et al., Eur. J. Immunol. 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a Neutrokine-α protein antigen or, more preferably, with a Neutrokine-α protein-expressing cell. Suitable cells can be recognized by their capacity to bind anti-Neutrokine-α protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the Neutrokine-α protein antigen.

Alternatively, additional antibodies capable of binding to the Neutrokine-α protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, Neutrokine-α-protein specific antibodies are used to immunize an animal, preferably a mouse. The splenocytes of such an animal are then used to produce hybridoma cells, and the hybridoma cells are screened to identify clones which produce an antibody whose ability to bind to the Neutrokine-α protein-specific antibody can be blocked by the Neutrokine-α protein antigen. Such antibodies comprise anti-idiotypic antibodies to the Neutrokine-α protein-specific antibody and can be used to immunize an animal to induce formation of further Neutrokine-α protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, Neutrokine-α protein-binding fragments can be produced through the application of recombinant DNA technology or through synthetic chemistry.

Where in vivo imaging is used to detect enhanced levels of Neutrokine-α protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *Bio-Techniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Treatment of Immune System-related Disorders

As noted above, Neutrokine-α polynucleotides and polypeptides are useful for diagnosis of conditions involving abnormally high or low expression of Neutrokine-α activities. Given the cells and tissues where Neutrokine-α is expressed as well as the activities modulated by Neutrokine-α, it is readily apparent that a substantially altered (increased or decreased) level of expression of Neutrokine-α in an individual compared to the standard or "normal" level produces pathological conditions related to the bodily system(s) in which Neutrokine-α is expressed and/or is active.

It will also be appreciated by one of ordinary skill that, since the Neutrokine-α protein of the invention is a member of the TNF family, the extracellular domain of the protein may be released in soluble form from the cells which express Neutrokine-α by proteolytic cleavage and therefore, when Neutrokine-α protein (particularly a soluble form of the extracellular domain) is added from an exogenous source to cells, tissues or the body of an individual, the protein will exert its modulating activities on any of its target cells of that individual. Also, cells expressing this type II transmembrane protein may be added to cells, tissues or the body of an individual whereby the added cells will bind to cells expressing receptor for Neutrokine-α whereby the cells expressing Neutrokine-α can cause actions (e.g., cytotoxicity) on the receptor-bearing target cells.

Therefore, it will be appreciated that conditions caused by a decrease in the standard or normal level of Neutrokine-α activity in an individual, particularly disorders of the immune system, can be treated by administration of Neutrokine-α protein (in the form of soluble extracellular domain or cells expressing the complete protein). Thus, the invention also provides a method of treatment of an individual in need of an increased level of Neutrokine-α activity comprising administering to such an individual a pharmaceutical composition comprising an amount of an isolated Neutrokine-α polypeptide of the invention, effective to increase the Neutrokine-α activity level in such an individual.

Since Neutrokine-α belongs to the TNF superfamily, it also should also modulate angiogenesis. In addition, since Neutrokine-α inhibits immune cell functions, it will have a wide range of anti-inflammatory activities. Neutrokine-α may be employed as an anti-neovascularizing agent to treat solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. Neutrokine-α may also be employed to inhibit T-cell proliferation by the inhibition of IL-2 biosynthesis for the treatment of T-cell mediated auto-immune diseases and lymphocytic leukemias. Neutrokine-α may also be employed to stimulate wound healing, both via the recruitment of debris clearing and connective tissue promoting inflammatory cells. In this same manner, Neutrokine-α may also be employed to treat other fibrotic disorders, including liver cirrhosis, osteoarthritis and pulmonary fibrosis. Neutrokine-α also increases the presence of eosinophils which have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. Neutrokine-α may also be employed to treat sepsis.

Formulations

The Neutrokine-α polypeptide composition (preferably containing a polypeptide which is a soluble form of the extracellular domain) will be formulated and dosed in a fashion consistent with good medical practice, taking into account the clinical condition of the individual patient (especially the side effects of treatment with Neutrokine-α polypeptide alone), the site of delivery of the Neutrokine-α polypeptide composition, the method of administration, the scheduling of administration, and other factors known to practitioners. The "effective amount" of Neutrokine-α polypeptide for purposes herein is thus determined by such considerations.

As a general proposition, the total pharmaceutically effective amount of Neutrokine-α polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Neutrokine-α polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the Neutrokine-α of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The Neutrokine-α polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release Neutrokine-α polypeptide compositions also include liposomally entrapped Neutrokine-α polypeptide. Liposomes containing Neutrokine-α polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Neutrokine-α polypeptide therapy.

For parenteral administration, in one embodiment, the Neutrokine-α polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Neutrokine α polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Neutrokine-α polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of Neutrokine-α polypeptide salts.

Neutrokine-α polypeptide to be used for therapeutic administration must be sterile. Sterility is readily accomplished by filtration through sterile filtration membranes (e.g., 0.2 micron membranes). Therapeutic Neutrokine-α polypeptide compositions generally are placed into a container having a sterile access port, for example, an intravenous solution bag or vial having a stopper pierceable by a hypodermic injection needle.

Neutrokine-α polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Neutrokine-α polypeptide solution, and the resulting mixture is lyophilized. The infusion solution is prepared by reconstituting the lyophilized Neutrokine-α polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of Neutrokine-α on cells, such as its interaction with Neutrokine-α binding molecules such as receptor molecules. An agonist is a compound which increases the natural biological functions of Neutrokine-α or which functions in a manner similar to Neutrokine while antagonists decrease or eliminate such functions.

In another aspect of this embodiment the invention provides a method for identifying a receptor protein or other ligand-binding protein which binds specifically to a Neutrokine-α polypeptide. For example, a cellular compartment, such as a membrane or a preparation thereof, may be prepared from a cell that expresses a molecule that binds Neutrokine-α. The preparation is incubated with labeled Neutrokine-α and complexes of Neutrokine-α bound to the receptor or other binding protein are isolated and characterized according to routine methods known in the art. Alternatively, the Neutrokine-α polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds Neutrokine-α such as a molecule of a signaling or regulatory pathway modulated by Neutrokine-α. The preparation is incubated with labeled Neutrokine-α in the absence or the presence of a candidate molecule which may be a Neutrokine-α agonist or antagonist. The ability of the candidate molecule to bind the binding molecule is reflected in decreased binding of the labeled ligand. Molecules which bind gratuitously, i.e., without inducing the effects of Neutrokine-α on binding the Neutrokine-α binding molecule, are most likely to be good antagonists. Molecules that bind well and elicit effects that are the same as or closely related to Neutrokine-α are agonists.

Neutrokine-α-like effects of potential agonists and antagonists may by measured, for instance, by determining activity of a second messenger system following interaction of the candidate molecule with a cell or appropriate cell preparation, and comparing the effect with that of Neutrokine-α or molecules that elicit the same effects as Neutrokine-α. Second messenger systems that may be useful in this regard include but are not limited to AMP guanylate cyclase, ion channel or phosphoinositide hydrolysis second messenger systems.

Another example of an assay for Neutrokine-α antagonists is a competitive assay that combines Neutrokine-α and a potential antagonist with membrane-bound receptor molecules or recombinant Neutrokine-α receptor molecules under appropriate conditions for a competitive inhibition assay. Neutrokine-α can be labeled, such as by radioactivity, such that the number of Neutrokine-α molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing Neutrokine-α induced activities, thereby preventing the action of Neutrokine-α by excluding Neutrokine-α from binding.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the extracellular domain of the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Neutrokine-α. The antisense RNA oligonucleotide hybridizes to the mRNA in vivo and blocks translation of the mRNA molecule into Neutrokine-α polypeptide. The oligonucleotides described above can also be delivered to cells such that the antisense RNA or DNA may be expressed in vivo to inhibit production of Neutrokine-α.

The agonists and antagonists may be employed in a composition with a pharmaceutically acceptable carrier, e.g., as described above.

The antagonists may be employed for instance to inhibit Neutrokine-α the chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the human chemokine polypeptides of the present invention. The antagonists may also be employed for treating atherosclerosis, by preventing monocyte infiltration in the artery wall. The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines. The antagonists may also be employed to treat cases of bone marrow failure, for example, aplastic anemia and myelodysplastic syndrome. The antagonists may also be employed to treat asthma and allergy by preventing eosinophil accunulation in the lung. The antagonists may also be employed to treat subepithelial basement membrane fibrosis which is a prominent feature of the asthmatic lung.

Antibodies against Neutrokine-α may be employed to bind to and inhibit Neutrokine-α activity to treat ARDS, by preventing infiltration of neutrophils into the lung after injury. The antagonists may be employed in a composition with a pharmaceutically acceptable carrier, e.g., as hereinafter described.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a Neutrokine-α protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1a

Expression and Purification of "His-tagged" Neurokine-α in *E. coli*

The bacterial expression vector pQE9 (pD10) is used for bacterial expression in this example. (QIAGEN, Inc., supra). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6× His tag") covalently linked to the amino terminus of that polypeptide.

The DNA sequence encoding the desired portion of the Neurokine-α protein comprising the extracellular domain sequence is amplified from the deposited cDNA clone using PCR oligonucleotide primers which anneal to the amino terminal sequences of the desired portion of the Neurokine-α protein and to sequences in the deposited construct 3' to the cDNA coding sequence. Additional nucleotides containing restriction sites to facilitate cloning in the pQE9 vector are added to the 5' and 3' primer sequences, respectively.

For cloning the extracellular domain of the protein, the 5' primer has the sequence 5' GTG GGA TCC GC CTC CGG GCA GAG CTG 3' (SEQ ID NO:10) containing the underlined BamHI restriction site followed by 18 nucleotides of the amino terminal coding sequence of the extracellular domain of the Neurokine-α sequence in FIGS. 1A and 1B. One of ordinary skill in the art would appreciate, of course, that the point in the protein coding sequence where the 5' primer begins may be varied to amplify a DNA segment encoding any desired portion of the complete Neutrokine Δ protein shorter or longer than the extracellular domain of the form. The 3' primer has the sequence 5'-GTG AAG CTT TTA TTA CAG CAG TTT CAA TGC ACC-3' (SEQ ID NO:11) containing the underlined HindIII restriction site followed by two stop codons and 18 nucleotides complementary to the 3' end of the coding sequence of the Neurokine-α DNA sequence in FIGS. 1A and 1B.

The amplified Neurokine-α DNA fragment and the vector pQE9 are digested with BamHI and HindIII and the digested DNAs are then ligated together. Insertion of the Neurokine-α DNA into the restricted pQE9 vector places the Neurokine-α protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing Neurokine-α protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing. Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the Neurokine-α is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6M guanidine-HCl, pH 8, the column is first washed with 10 volumes of 6M guanidine-HCl, pH 8, then washed with 10 volumes of 6M guanidine-HCl pH 6, and finally the Neurokine-α is eluted with 6M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Example 1b

Expression and Purification of Neutrokine-α in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the Neurokine-α protein comprising the extracellular domain sequence is amplified from the deposited cDNA clone using PCR oligonucleotide primers which anneal to the amino terminal sequences of the desired portion of the Neurokine-α protein and to sequences in the deposited construct 3' to the cDNA coding sequence. Additional nucleotides containing restriction sites to facilitate cloning in the pQE60 vector are added to the 5' and 3' sequences, respectively.

For cloning the extracellular domain of the protein, the 5' primer has the sequence 5' GTG TCA TGA GCC TCC GGG CAG AGC TG 3' (SEQ ID NO:12) containing the underlined BspHI restriction site followed by 17 nucleotides of the amino terminal coding sequence of the extracellular domain of the Neurokine-α sequence in FIGS. 1A and 1B. One of ordinary skill in the art would appreciate, of course, that the point in the protein coding sequence where the 5' primer begins may be varied to amplify a desired portion of the complete protein shorter or longer than the extracellular domain of the form. The 3' primer has the sequence 5'-GTG AAG CTT TTA TTA CAG CAG TTT CAA TGC ACC 3' (SEQ ID NO:13) containing the underlined HindIII restriction site followed by two stop codons and 18 nucleotides complementary to the 3' end of the coding sequence in the Neurokine-α DNA sequence in FIGS. 1A and 1B.

The amplified Neurokine-α DNA fragments and the vector pQE60 are digested with BspHI and HindIII and the digested DNAs are then ligated together. Insertion of the Neurokine-α DNA into the restricted pQE60 vector places the Neurokine-α protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing Neurokine-α protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

One of ordinary skill in the art recognizes that any of a number of bacterial expression vectors may be useful in place of pQE9 and pQE60 in the expression protocols presented in this example. For example, the novel pHE4 series of bacterial expression vectors, in particular, the pHE4-5 vector may be used for bacterial expression in this example (ATCC Accession No. 209311; and variations thereof). The plasmid DNA designated pHE4-5/MPIFΔ23 in ATCC Deposit No. 209311 is vector plasmid DNA which contains an insert which encodes another ORF. The construct was deposited with the American Type Culture Collection, 12301 Park Lawn Drive, Rockville, Md. 20852, on Sep. 30, 1997. Using the NdeI and Asp 718 restriction sites flanking the irrelevant MPIF ORF insert, one of ordinary skill in the art could easily use current molecular biological techniques to replace the irrelevant ORF in the pHE4-5 vector with the Neurokine-α ORF of the present invention.

The pHE4-5 bacterial expression vector includes a neomycin phosphotransferase gene for selection, an *E. coli* origin of replication, a T5 phage promoter sequence, two lac operator sequences, a Shine-Delgarno sequence, and the lactose operon repressor gene (lacIq). These elements are arranged such that an inserted DNA fragment encoding a polypeptide expresses that polypeptide with the six His residues (i.e., a "6×His tag") covalently linked to the amino terminus of that polypeptide. The promoter and operator sequences of the pHE4-5 vector were made synthetically. Synthetic production of nucleic acid sequences is well known in the art (CLONETECH 95/96 Catalog, pages 215–216, CLONETECH, 1020 East Meadow Circle, Palo Alto, Calif. 94303).

Clones containing the desired Neurokine-α constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the Neutrokine α is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure Neurokine-α protein. The purified protein is stored at 4° C. or frozen at −80° C.

Example 2

Cloning and Expression of Neutrokine-α Protein in a Baculovirus Expression System In this illustrative example, the plasmid shuttle vector pA2GP is used to insert the cloned DNA encoding the extracellular domain of the protein, lacking its naturally associated intracellular and transmembrane sequences, into a baculovirus to express the extracellular domain of the Neurokine-α protein, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the extracellular domain of the Neurokine-α protein in the deposited clone, lacking the AUG initiation codon and the naturally associated intracellular and transmembrane domain sequences shown in FIGS. 1A and 1B (SEQ ID NO:2), is amplified using PCR oligonucleotide primers corresponding to the 5' and 3' sequences of the gene. The 5' primer has the sequence 5'-GTG <u>GGA TCC</u> CCG GGC AGA GCT GCA GGG C-3' (SEQ ID NO:14) containing the underlined BamHI restriction enzyme site followed by 18 nucleotides of the sequence of the extracellular domain of the Neurokine-α protein shown in FIGS. 1A and 1B, beginning with the indicated N-terminus of the extracellular domain of the protein. The 3' primer has the sequence 5'-GTG <u>GGA TCC</u> TTA TTA CAG CAG TTT CAA TGC ACC-3' (SEQ ID NO:15) containing the underlined BamHI restriction site followed by two stop codons and 18 nucleotides complementary to the 3' coding sequence in FIGS. 1A and 1B.

The amplified fragment is isolated from a 1% agarose gel using a commercially available kit ("Geneclean," BIO 101 Inc., La Jolla, Calif.). The fragment then is digested with BamHI and again is purified on a 1% agarose gel. This fragment is designated herein F1.

The plasmid is digested with the restriction enzymes BamHI and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human Neurokine-α gene by digesting DNA from individual colonies using BamHI and then analyzing the digestion product by gel electrophoresis. The sequence of the cloned fragment is confirmed by DNA sequencing. This plasmid is designated herein pA2GP-Neutrokine-α.

Five μg of the plasmid pA2GP-Neutrokine-α is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). One μg of BaculoGold™ virus DNA and 5 μg of the plasmid pA2GP Neurokine-α are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 ∞l of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Neurokine-α.

To verify the expression of the Neurokine-α gene Sf9 cells are grown in Grace's medium supplemented with 10% heat-inactivated FBS. The cells are infected with the recombinant baculovirus V-Neurokine-α at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the extracellular domain of the protein and thus the cleavage point and length of the secretory signal peptide.

Example 3

Cloning and Expression of Neutrokine-α in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BamHI, XbaI and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pNeurokine-α-HA, is made by cloning a portion of the deposited cDNA encoding the extracellular domain of the Neurokine-α protein into the expression vector pcDNAI/Amp or pcDNAIII (which can be obtained from Invitrogen, Inc.). To produce a soluble, secreted form of the polypeptide, the extracellular domain is fused to the secretory leader sequence of the human IL-6 gene.

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the extracellular domain of the Neurokine-α polypeptide is cloned into the polylinker region of the vector so that recombinant protein expression is directed by the CMV promoter. The plasmid construction strategy is as follows. The Neurokine-α cDNA of the deposited clone is amplified using primers that contain convenient restriction sites, much as described above for construction of vectors for expression of Neurokine-α in *E. coli*. Suitable primers include the following, which are used in this example. The 5' primer, containing the underlined BamHI site, a Kozak sequence, an AUG start codon, a sequence encoding the secretory leader peptide from the human IL-6 gene, and 18 nucleotides of the 5' coding region of the extracellular domain of Neurokine-α protein, has the following sequence: 5'-GCG <u>GGA TCC</u> GCC ACC ATG AAC TCC TTC TCC ACA AGC GCC TTC GGT CCA GTT GCC TTC TCC CTG GGG CTG CTC CTG GTG TTG CCT GCT GCC TTC CCT GCC CCA GTT GTG AGA CAA GGG GAC CTG GCC AGC-3' (SEQ ID NO:16). The 3' primer, containing the underlined BamHI restriction site and 18 of nucleotides complementary to the 3' coding sequence immediately before the stop codon, has the following sequence: 5'-GTG <u>GGA TCC</u> TTA CAG CAG TTT CAA TGC ACC-3' (SEQ ID NO:17).

The PCR amplified DNA fragment and the vector, pcDNAI/Amp, are digested with BamHI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the Neutrokine-α extracellular domain.

For expression of recombinant Neurokine-α, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of Neurokine-α by the vector.

Expression of the Neurokine-α-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of Neurokine-α protein. Plasmid pC4 is a derivative of the plasmid pSV2-dhfr (ATCC Accession No. 37146). To produce a soluble, secreted form of the Neurokine-α polypeptide, the portion of the deposited cDNA encoding the extracellular domain is fused to the secretory leader sequence of the human IL-6 gene. The vector plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, XbaI, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the Neurokine-α in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and then dephosphorylated using calf intestinal phosphates by procedures known in the art. The vector is then isolated from a 1% agarose gel.

The DNA sequence encoding the extracellular domain of the Neurokine-α protein is amplified using PCR oligonucleotide primers corresponding to the 5' and 3' sequences of the gene. The 5' primer, containing the underlined BamHI site, a Kozak sequence, an AUG start codon, a sequence encoding the secretory leader peptide from the human IL-6 gene, and 18 nucleotides of the 5' coding region of the extracellular domain of Neurokine-α protein, has the following sequence: 5'-GCG GGA TCC <u>GCCACC</u> ATG AAC TCC TTC TCC ACA AGC GCC TTC GGT CCA GTT GCC TTC TCC CTG GGG CTG CTC CTG GTG TTG CCT GCT GCC TTC CCT GCC CCA GTT GTG AGA CAA GGG GAC CTG GCC AGC-3' (SEQ ID NO:16). The 3' primer, containing the underlined BamHI and 18 of nucleotides complementary to the 3' coding sequence immediately before the stop codon, has the following sequence: 5'-GTG <u>GGA TCC</u> TTA CAG CAG TTT CAA TGC ACC-3' (SEQ ID NO:17).

The amplified fragment is digested with the endonuclease BamHI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue Distribution of Neurokine-α mRNA Expression

Northern blot analysis is carried out to examine Neurokine-α gene expression in human tissues, using methods described by, among others, Sambrook et al., cited above. A cDNA probe containing the entire nucleotide sequence of the Neutrokine-α protein (SEQ ID NO:1) is labeled with ³²P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for Neutrokine-α mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a first polynucleotide sequence at least 95% identical to a second polynucleotide sequence selected from the group consisting of:
   (a) a polynucleotide sequence encoding the Neutrokine-α polypeptide having the complete amino acid sequence in FIGS. 1A and B (SEQ ID NO:2);
   (b) a polynucleotide sequence encoding the Neutrokine-α polypeptide having the complete amino acid sequence encoded by the cDNA clone contained in ATCC No. 97768 deposited on Oct. 22, 1996;
   (c) a polynucleotide sequence encoding the Neutrokine-α polypeptide extracellular domain;
   (d) a polynucleotide sequence encoding a soluble Neutrokine-α polypeptide comprising the extracellular and intracellular domains but lacking the transmembrane domain; and
   (e) a polynucleotide sequence complementary to the full length of any of the polynucleotide sequences in (a), (b), (c) or (d) above;
   wherein said first polynucleotide encodes a polypeptide that stimulates B lymphocyte proliferation, differentiation, or survival.

2. An isolated nucleic acid molecule comprising a polynucleotide sequence selected from the group consisting of:
   (a) a polynucleotide sequence encoding amino acid residues 1 to 285 of SEQ ID NO:2;
   (b) a polynucleotide sequence encoding amino acid residues 2 to 285 of SEQ ID NO:2;
   (c) a polynucleotide sequence encoding a fragment of the Neutrokine-α polypeptide of SEQ ID NO:2, wherein the fragment stimulates B lymphocyte proliferation, differentiation, or survival;
   (d) a polynucleotide sequence encoding the full-length Neutrokine-α having the amino acid sequence encoded by the cDNA clone contained in ATCC Deposit No. 97768;
   (e) a polynucleotide sequence encoding the full-length Neutrokine-α, excluding the N-terminal methionine residue, having the amino acid sequence encoded by the cDNA clone contained in ATCC Deposit No. 97768;
   (f) a polynucleotide sequence encoding a fragment of Neutrokine-α having the amino acid sequence encoded by the cDNA clone contained in ATCC Deposit No. 97768, wherein the fragment stimulates B lymphocyte proliferation, differentiation, or survival; and
   (g) a polynucleotide sequence complementary to the full length of any of the polynucleotide sequences in (a), (b), (c), (d), (e) or (f) above.

3. The isolated nucleic acid molecule of claim 2 which comprises polynucleotide sequence (a).

4. The isolated nucleic acid molecule of claim 3 which comprises nucleotides 147 to 1001 of SEQ ID NO:1.

5. The isolated nucleic acid molecule of claim 2 which comprises polynucleotide sequence (b).

6. The isolated nucleic acid molecule of claim 5 which comprises nucleotides 150 to 1001 of SEQ ID NO:1.

7. The isolated nucleic acid molecule of claim 2 which comprises polynucleotide sequence (c).

8. The isolated nucleic acid molecule of claim 7 wherein the fragment stimulates B lymphocyte proliferation.

9. The isolated nucleic acid molecule of claim 7 wherein the fragment stimulates B lymphocyte differentiation.

10. The isolated nucleic acid molecule of claim 2 which comprises polynucleotide sequence (d).

11. The isolated nucleic acid molecule of claim 2 which comprises polynucleotide sequence (e).

12. The isolated nucleic acid molecule of claim 2 which comprises polynucleotide sequence (f).

13. The isolated nucleic acid molecule of claim 12 wherein the fragment stimulates B lymphocyte proliferation.

14. The isolated nucleic acid molecule of claim 12 wherein the fragment stimulates B lymphocyte differentiation.

15. The isolated nucleic acid molecule of claim 2 which comprises polynucleotide sequence (g).

16. An isolated nucleic acid molecule comprising a polynucleotide sequence selected from the group consisting of:
   (a) a polynucleotide sequence encoding amino acid residues 73 to 285 of SEQ ID NO:2; and
   (b) a polynucleotide sequence complementary to the full length of the polynucleotide sequence in (a).

17. The isolated nucleic acid molecule of claim 16 which comprises polynucleotide sequence (a).

18. The isolated nucleic acid molecule of claim 16 which comprises polynucleotide sequence (b).

19. The isolated nucleic acid molecule of claim 17 which comprises nucleotides 363 to 1001 of SEQ ID NO:1.

20. The isolated nucleic acid molecule of claim 17 which further comprises a polynucleotide sequence encoding amino acid residues 1–46 of SEQ ID NO:2.

21. The isolated nucleic acid molecule of claim 17 which further comprises a polynucleotide sequence encoding amino acid residues 47–72 of SEQ ID NO:2.

22. An isolated nucleic acid molecule comprising a polynucleotide sequence encoding amino acid residues 191 to 284 of SEQ ID NO:2, wherein the polynucleotide sequence encodes a polypeptide which can be used to generate or select for an antibody that specifically binds the polypeptide of SEQ ID NO:2.

23. The isolated nucleic acid molecule of claim 22 which comprises nucleotides 717 to 998 of SEQ ID NO:1.

24. The isolated nucleic acid molecule of claim 22 which consists of a polynucleotide sequence encoding amino acid residues 191 to 284 of SEQ ID NO:2.

25. The isolated nucleic acid molecule of claim 22 which consists of nucleotides 717 to 998 of SEQ ID NO:1.

26. An isolated nucleic acid molecule comprising a polynucleotide sequence encoding amino acid residues 168 to 285 of SEQ ID NO:2, wherein the polynucleotide sequence encodes a polypeptide which can be used to generate or select for an antibody that specifically binds the polypeptide of SEQ ID NO:2.

27. The isolated nucleic acid molecule of claim 26 which comprises nucleotides 648 to 1001 of SEQ ID NO:1.

28. The isolated nucleic acid molecule of claim 26 which consists of a polynucleotide sequence encoding amino acid residues 168 to 285 of SEQ ID NO:2.

29. The isolated nucleic acid molecule of claim 26 which consists of nucleotides 648 to 1001 of SEQ ID NO:1.

30. The isolated nucleic acid molecule of claim 26 which consists of a polynucleotide sequence encoding amino acid residues 168 to 285 of SEQ ID NO:2 preceded immediately by an N-terminal methionine.

31. The isolated nucleic acid molecule of claim 26 which consists of nucleotides 648 to 1001 of SEQ ID NO:1 preceded immediately by nucleotides 5'-ATG-3'.

32. An isolated nucleic acid molecule comprising a polynucleotide sequence encoding amino acid residues 134 to 285 of SEQ ID NO:2.

33. The isolated nucleic acid molecule of claim 32 which comprises nucleotides 546 to 1001 of SEQ ID NO:1.

34. The isolated nucleic acid molecule of claim 32 which consists of a polynucleotide sequence encoding amino acid residues 134 to 285 of SEQ ID NO:2.

35. The isolated nucleic acid molecule of claim 32 which consists of nucleotides 546 to 1001 of SEQ ID NO:1.

36. The isolated nucleic acid molecule of claim 32 which consists of a polynucleotide sequence encoding amino acid residues 134 to 285 of SEQ ID NO:2 preceded immediately by an N-terminal methionine residue.

37. The isolated nucleic acid molecule of claim 32 which consists of nucleotides 546 to 1001 of SEQ ID NO:1 preceded immediately by nucleotides 5'-ATG-3'.

38. An isolated nucleic acid molecule comprising a polynucleotide sequence encoding amino acid residues 112 to 285 of SEQ ID NO:2.

39. The isolated nucleic acid molecule of claim 38 which comprises nucleotides 480 to 1001 of SEQ ID NO:1.

40. The isolated nucleic acid molecule of claim 38 which consists of a polynucleotide sequence encoding amino acid residues 112 to 285 of SEQ ID NO:2.

41. The isolated nucleic acid molecule of claim 38 which consists of nucleotides 480 to 1001 of SEQ ID NO:1.

42. The isolated nucleic acid molecule of claim 38 which consists of a polynucleotide sequence encoding amino acid residues 112 to 285 of SEQ ID NO:2 preceded immediately by an N-terminal methionine residue.

43. The isolated nucleic acid molecule of claim 38 which consists of nucleotides 480 to 1001 of SEQ ID NO:1 preceded immediately by nucleotides 5'-ATG-3'.

44. An isolated nucleic acid molecule comprising a polynucleotide sequence encoding amino acid residues 81 to 285 of SEQ ID NO:2.

45. The isolated nucleic acid molecule of claim 44 which comprises nucleotides 387 to 1001 of SEQ ID NO:1.

46. The isolated nucleic acid molecule of claim 44 which consists of a polynucleotide sequence encoding amino acid residues 81 to 285 of SEQ ID NO:2.

47. The isolated nucleic acid molecule of claim 44 which consists of nucleotides 387 to 1001 of SEQ ID NO:1.

48. The isolated nucleic acid molecule of claim 44 which consists of a polynucleotide sequence encoding amino acid residues 81 to 285 of SEQ ID NO:2 preceded immediately by an N-terminal methionine residue.

49. The isolated nucleic acid molecule of claim 44 which consists of nucleotides 387 to 1001 of SEQ ID NO:1 preceded immediately by nucleotides 5'-ATG-3'.

50. An isolated nucleic acid molecule comprising a polynucleotide sequence encoding amino acid residues 71 to 285 of SEQ ID NO:2.

51. The isolated nucleic acid molecule of claim 50 which comprises nucleotides 357 to 1001 of SEQ ID NO:1.

52. The isolated nucleic acid molecule of claim 50 which consists of a polynucleotide sequence encoding amino acid residues 71 to 285 of SEQ ID NO:2.

53. The isolated nucleic acid molecule of claim 50 which consists of nucleotides 357 to 1001 of SEQ ID NO:1.

54. The isolated nucleic acid molecule of claim 50 which consists of a polynucleotide sequence encoding amino acid residues 71 to 285 of SEQ ID NO:2 preceded immediately by an N-terminal methionine residue.

55. The isolated nucleic acid molecule of claim 50 which consists of nucleotides 357 to 1001 of SEQ ID NO:1 preceded immediately by nucleotides 5'-ATG-3'.

56. An isolated nucleic acid molecule comprising a polynucleotide sequence that encodes a polypeptide comprising an amino acid sequence that is 90% or more identical to the amino acid sequence of amino acid residues 134 to 285 of SEQ ID NO:2;

wherein the polypeptide stimulates B lymphocyte proliferation, differentiation, or survival.

57. An isolated nucleic acid molecule comprising a polynucleotide which hybridizes to the complement of the full-length Neutrokine-α polynucleotide shown as SEQ ID NO:1, wherein said hybridization occurs under conditions consisting of hybridization in a solution consisting of 50% formamide, 5× SSC, 50 mM sodium phosphate (pH 7.6), 5× Denhardt's solution, 10% dextran sulfate, and 20 μg/ml denature, sheared salmon sperm DNA overnight at 42° C. and wash in a solution consisting of 0.1× SSC at 65° C.; and wherein said hybridizing polynucleotide encodes a polypeptide which stimulates B lymphocyte proliferation, differentiation, or survival.

58. The isolated nucleic acid molecule of claim 2 wherein the polynucleotide sequence further comprises a heterologous polynucleotide sequence.

59. The isolated nucleic acid molecule of claim 58 wherein the heterologous polynucleotide sequence encodes a heterologous polypeptide.

60. The isolated nucleic acid molecule of claim 59 wherein the heterologous polypeptide is the Fc domain of human immunoglobulin.

61. A recombinant vector comprising the isolated nucleic acid molecule of claim 2.

62. The recombinant vector of claim 61 wherein the nucleic acid molecule is operably associated with a heterologous regulatory sequence that controls gene expression.

63. A recombinant host cell comprising the isolated nucleic acid molecule of claim 2.

64. The recombinant host cell of claim 63 wherein the nucleic acid molecule is operably associated with a heterologous regulatory sequence that controls gene expression.

65. A method for producing a polypeptide, comprising:
(a) culturing a host cell under conditions suitable to produce a polypeptide encoded by the nucleic acid molecule of claim 2; and (b) recovering the polypeptide from the cell culture.

66. The isolated nucleic acid molecule of claim 16 wherein the polynucleotide sequence further comprises a heterologous polynucleotide sequence.

67. The isolated nucleic acid molecule of claim 66 wherein the heterologous polynucleotide sequence encodes a heterologous polypeptide.

68. The isolated nucleic acid molecule of claim 67 wherein the heterologous polypeptide is the Fc domain of human immunoglobulin.

69. A recombinant vector comprising the isolated nucleic acid molecule of claim 16.

70. The recombinant vector of claim 69 wherein the nucleic acid molecule is operably associated with a heterologous regulatory sequence that controls gene expression.

71. A recombinant host cell comprising the isolated nucleic acid molecule of claim 16.

72. The recombinant host cell of claim 71 wherein the nucleic acid molecule is operably associated with a heterologous regulatory sequence that controls gene expression.

73. A method for producing a polypeptide, comprising:
(a) culturing a host cell under conditions suitable to produce a polypeptide encoded by the nucleic acid molecule of claim 16; and
(b) recovering the polypeptide from the cell culture.

74. The isolated nucleic acid molecule of claim 22 wherein the polynucleotide sequence further comprises a heterologous polynucleotide sequence.

75. The isolated nucleic acid molecule of claim 74 wherein the heterologous polynucleotide sequence encodes a heterologous polypeptide.

76. The isolated nucleic acid molecule of claim 75 wherein the heterologous polypeptide is the Fc domain of human immunoglobulin.

77. A recombinant vector comprising the isolated nucleic acid molecule of claim 22.

78. The recombinant vector of claim 77 wherein the nucleic acid molecule is operably associated with a heterologous regulatory sequence that controls gene expression.

79. A recombinant host cell comprising the isolated nucleic acid molecule of claim 22.

80. The recombinant host cell of claim 79 wherein the nucleic acid molecule is operably associated with a heterologous regulatory sequence that controls gene expression.

81. A method for producing a polypeptide, comprising:
(a) culturing a host cell under conditions suitable to produce a polypeptide encoded by the nucleic acid molecule of claim 22; and
(b) recovering the polypeptide from the cell culture.

82. The isolated nucleic acid molecule of claim 26 wherein the polynucleotide sequence further comprises a heterologous polynucleotide sequence.

83. The isolated nucleic acid molecule of claim 82 wherein the heterologous polynucleotide sequence encodes a heterologous polypeptide.

84. The isolated nucleic acid molecule of claim 83 wherein the heterologous polypeptide is the Fc domain of human immunoglobulin.

85. A recombinant vector comprising the isolated nucleic acid molecule of claim 26.

86. The recombinant vector of claim 85 wherein the nucleic acid molecule is operably associated with a heterologous regulatory sequence that controls gene expression.

87. A recombinant host cell comprising the isolated nucleic acid molecule of claim 26.

88. The recombinant host cell of claim 87 wherein the nucleic acid molecule is operably associated with a heterologous regulatory sequence that controls gene expression.

89. A method for producing a polypeptide, comprising:
(a) culturing a host cell under conditions suitable to produce a polypeptide encoded by the nucleic acid molecule of claim 26; and
(b) recovering the polypeptide from the cell culture.

90. The isolated nucleic acid molecule of claim 32 wherein the polynucleotide sequence further comprises a heterologous polynucleotide sequence.

91. The isolated nucleic acid molecule of claim 90 wherein the heterologous polynucleotide sequence encodes a heterologous polypeptide.

92. The isolated nucleic acid molecule of claim 91 wherein the heterologous polypeptide is the Fc domain of human immunoglobulin.

93. A recombinant vector comprising the isolated nucleic acid molecule of claim 32.

94. The recombinant vector of claim 93 wherein the nucleic acid molecule is operably associated with a heterologous regulatory sequence that controls gene expression.

95. A recombinant host cell comprising the isolated nucleic acid molecule of claim 32.

96. The recombinant host cell of claim 95 wherein the nucleic acid molecule is operably associated with a heterologous regulatory sequence that controls gene expression.

97. A method for producing a polypeptide, comprising:
(a) culturing a host cell under conditions suitable to produce a polypeptide encoded by the nucleic acid molecule of claim 32; and
(b) recovering the polypeptide from the cell culture.

98. The isolated nucleic acid molecule of claim 38 wherein the polynucleotide sequence further comprises a heterologous polynucleotide sequence.

99. The isolated nucleic acid molecule of claim 98 wherein the heterologous polynucleotide sequence encodes a heterologous polypeptide.

100. The isolated nucleic acid molecule of claim 99 wherein the heterologous polypeptide is the Fc domain of human immunoglobulin.

101. A recombinant vector comprising the isolated nucleic acid molecule of claim 38.

102. The recombinant vector of claim 101 wherein the nucleic acid molecule is operably associated with a heterologous regulatory sequence that controls gene expression.

103. A recombinant host cell comprising the isolated nucleic acid molecule of claim 38.

104. The recombinant host cell of claim 103 wherein the nucleic acid molecule is operably associated with a heterologous regulatory sequence that controls gene expression.

105. A method for producing a polypeptide, comprising:
(a) culturing a host cell under conditions suitable to produce a polypeptide encoded by the nucleic acid molecule of claim 38; and
(b) recovering the polypeptide from the cell culture.

106. The isolated nucleic acid molecule of claim 44 wherein the polynucleotide sequence further comprises a heterologous polynucleotide sequence.

107. The isolated nucleic acid molecule of claim 106 wherein the heterologous polynucleotide sequence encodes a heterologous polypeptide.

108. The isolated nucleic acid molecule of claim 107 wherein the heterologous polypeptide is the Fc domain of human immunoglobulin.

109. A recombinant vector comprising the isolated nucleic acid molecule of claim 44.

110. The recombinant vector of claim 109 wherein the nucleic acid molecule is operably associated with a heterologous regulatory sequence that controls gene expression.

111. A recombinant host cell comprising the isolated nucleic acid molecule of claim 44.

112. The recombinant host cell of claim 111 wherein the nucleic acid molecule is operably associated with a heterologous regulatory sequence that controls gene expression.

113. A method for producing a polypeptide, comprising:
(a) culturing a host cell under conditions suitable to produce a polypeptide encoded by the nucleic acid molecule of claim 44; and
(b) recovering the polypeptide from the cell culture.

114. The isolated nucleic acid molecule of claim 50 wherein the polynucleotide sequence further comprises a heterologous polynucleotide sequence.

115. The isolated nucleic acid molecule of claim 114 wherein the heterologous polynucleotide sequence encodes a heterologous polypeptide.

116. The isolated nucleic acid molecule of claim 115 wherein the heterologous polypeptide is the Fc domain of human immunoglobulin.

117. A recombinant vector comprising the isolated nucleic acid molecule of claim 50.

118. The recombinant vector of claim 117 wherein the nucleic acid molecule is operably associated with a heterologous regulatory sequence that controls gene expression.

119. A recombinant host cell comprising the isolated nucleic acid molecule of claim 50.

120. The recombinant host cell of claim 119 wherein the nucleic acid molecule is operably associated with a heterologous regulatory sequence that controls gene expression.

121. A method for producing a polypeptide, comprising:
(a) culturing a host cell under conditions suitable to produce a polypeptide encoded by the nucleic acid molecule of claim 50; and
(b) recovering the polypeptide from the cell culture.

122. The isolated nucleic acid molecule of claim 56 wherein the polynucleotide sequence further comprises a heterologous polynucleotide sequence.

123. The isolated nucleic acid molecule of claim 122 wherein the heterologous polynucleotide sequence encodes a heterologous polypeptide.

124. The isolated nucleic acid molecule of claim 123 wherein the heterologous polypeptide is the Fc domain of human immunoglobulin.

125. A recombinant vector comprising the isolated nucleic acid molecule of claim 56.

126. The recombinant vector of claim 125 wherein the nucleic acid molecule is operably associated with a heterologous regulatory sequence that controls gene expression.

127. A recombinant host cell comprising the isolated nucleic acid molecule of claim 56.

128. The recombinant host cell of claim 127 wherein the nucleic acid molecule is operably associated with a heterologous regulatory sequence that controls gene expression.

129. A method for producing a polypeptide, comprising:
(a) culturing a host cell under conditions suitable to produce a polypeptide encoded by the nucleic acid molecule of claim 56; and
(b) recovering the polypeptide from the cell culture.

130. The isolated nucleic acid molecule of claim 57 wherein the polynucleotide sequence further comprises a heterologous polynucleotide sequence.

131. The isolated nucleic acid molecule of claim 130 wherein the heterologous polynucleotide sequence encodes a heterologous polypeptide.

132. The isolated nucleic acid molecule of claim 131 wherein the heterologous polypeptide is the Fc domain of human immunoglobulin.

133. A recombinant vector comprising the isolated nucleic acid molecule of claim 57.

134. The recombinant vector of claim 133 wherein the nucleic acid molecule is operably associated with a heterologous regulatory sequence that controls gene expression.

135. A recombinant host cell comprising the isolated nucleic acid molecule of claim 57.

136. The recombinant host cell of claim 135 wherein the nucleic acid molecule is operably associated with a heterologous regulatory sequence that controls gene expression.

137. A method for producing a polypeptide, comprising:
(a) culturing a host cell under conditions suitable to produce a polypeptide encoded by the nucleic acid molecule of claim 57; and
(b) recovering the polypeptide from the cell culture.

138. The isolated nucleic acid molecule of claim 56 wherein the polynucleotide sequence encodes a polypeptide comprising an amino acid sequence that is 95% or more identical to the amino acid sequence of amino acid residues 134 to 285 of SEQ ID NO:2.

139. The isolated nucleic acid molecule of claim 57 wherein the polypeptide stimulates B lymphocyte proliferation.

140. The isolated nucleic acid molecule of claim 57 wherein the polypeptide stimulates B lymphocyte differentiation.

141. An isolated nucleic acid molecule comprising a polynucleotide sequence that encodes a polypeptide comprising an amino acid sequence that is 95% or more identical to an amino acid sequence selected from the group consisting of:
(a) the amino acid sequence of amino acid residues n to 285 of SEQ ID NO:2, where n is an integer in the range of 2–190;
(b) the amino acid sequence of amino acid residues 1 to m of SEQ ID NO:2, where m is an integer in the range of 274–284; and
(c) the amino acid sequence of amino acid residues n to m of SEQ ID NO:2, where n is an integer in the range of 2–190 and m is an integer in the range of 274–284;
wherein the polypeptide stimulates B lymphocyte proliferation, differentiation, or survival.

142. The isolated nucleic acid molecule of claim 141 which comprises a polynucleotide sequence that encodes a polypeptide comprising an amino acid sequence that is at least 95% identical to an amino acid sequence (a).

143. The isolated nucleic acid molecule of claim 141 which comprises a polynucleotide sequence that encodes a polypeptide comprising an amino acid sequence that is at least 95% identical to an amino acid sequence (b).

144. The isolated nucleic acid molecule of claim 141 which comprises a polynucleotide sequence that encodes a polypeptide comprising an amino acid sequence that is at least 95% identical to an amino acid sequence (c).

145. The isolated nucleic acid molecule of claim 141 wherein the polynucleotide sequence further comprises a heterologous polynucleotide sequence.

146. The isolated nucleic acid molecule of claim 145 wherein the heterologous polynucleotide sequence encodes a heterologous polypeptide.

147. The isolated nucleic acid molecule of claim 146 wherein the heterologous polypeptide is the Fc domain of human immunoglobulin.

148. A recombinant vector comprising the isolated nucleic acid molecule of claim 141.

149. The recombinant vector of claim 148 wherein the nucleic acid molecule is operably associated with a heterologous regulatory sequence that controls gene expression.

150. A recombinant host cell comprising the isolated nucleic acid molecule of claim 141.

151. The recombinant host cell of claim 150 wherein the nucleic acid molecule is operably associated with a heterologous regulatory sequence that controls gene expression.

152. A method for producing a polypeptide, comprising:
(a) culturing a host cell under conditions suitable to produce a polypeptide encoded by the nucleic acid molecule of claim 141; and
(b) recovering the polypeptide from the cell culture.

153. An isolated nucleic acid molecule comprising a polynucleotide sequence selected from the group consisting of:
(a) a polynucleotide sequence encoding a portion of the complete amino acid sequence encoded by the cDNA clone contained in ATCC Deposit Number 97768 wherein said portion excludes up to 190 contiguous amino acid residues from the amino terminus of said complete amino acid sequence;
(b) a polynucleotide sequence encoding a portion of the complete amino acid sequence encoded by the cDNA clone contained in ATCC Deposit Number 97768 wherein said portion excludes up to 11 contiguous amino acid residues from the carboxy terminus of said complete amino acid sequence; and
(c) a polynucleotide sequence encoding a portion of the complete amino acid sequence encoded by the cDNA clone contained in ATCC Deposit Number 97768 wherein said portion excludes up to 190 contiguous amino acid residues from the amino terminus and up to 11 contiguous amino acid residues from the carboxy terminus of said complete amino acid sequence;
wherein the polynucleotide sequence encodes a polypeptide which stimulates B lymphocyte proliferation, differentiation, or survival.

154. The isolated nucleic acid molecule of claim 153 which comprises polynucleotide sequence (a).

155. The isolated nucleic acid molecule of claim 153 which comprises polynucleotide sequence (b).

156. The isolated nucleic acid molecule of claim 153 which comprises polynucleotide sequence (c).

157. The isolated nucleic acid molecule of claim 153 wherein the polynucleotide sequence further comprises a heterologous polynucleotide sequence.

158. The isolated nucleic acid molecule of claim 157 wherein the heterologous polynucleotide sequence encodes a heterologous polypeptide.

159. The isolated nucleic acid molecule of claim 158 wherein the heterologous polypeptide is the Fc domain of human immunoglobulin.

160. A recombinant vector comprising the isolated nucleic acid molecule of claim 153.

161. The recombinant vector of claim 160 wherein the nucleic acid molecule is operably associated with a heterologous regulatory sequence that controls gene expression.

162. A recombinant host cell comprising the isolated nucleic acid molecule of claim 153.

163. The recombinant host cell of claim 162 wherein the nucleic acid molecule is operably associated with a heterologous regulatory sequence that controls gene expression.

164. A method for producing a polypeptide, comprising:
(a) culturing a host cell under conditions suitable to produce a polypeptide encoded by the nucleic acid molecule of claim 153; and
(b) recovering the polypeptide from the cell culture.

165. An isolated nucleic acid molecule comprising a polynucleotide sequence encoding a fragment of at least 30 contiguous amino acids of SEQ ID NO:2 wherein the fragment can be used to generate or select for an antibody that specifically binds the polypeptide of SEQ ID NO:2; or the complementary strand thereto.

166. The isolated nucleic acid molecule of claim 165 wherein said polynucleotide sequence encodes a fragment of at least 50 contiguous amino acids of SEQ ID NO:2.

167. The isolated nucleic acid molecule of claim 165, wherein said nucleic acid molecule comprises SEQ ID NO:1.

168. The isolated nucleic acid molecule of claim 165, wherein said nucleic acid molecule comprises a sequence complementary to the full length of SEQ ID NO:1.

169. The isolated nucleic acid molecule of claim 165 wherein the polynucleotide sequence further comprises a heterologous polynucleotide sequence.

170. The isolated nucleic acid molecule of claim 169 wherein the heterologous polynucleotide sequence encodes a heterologous polypeptide.

171. The isolated nucleic acid molecule of claim 170 wherein the heterologous polypeptide is the Fc domain of human immunoglobulin.

172. A recombinant vector comprising the isolated nucleic acid molecule of claim 165.

173. The recombinant vector of claim 172 wherein the nucleic acid molecule is operably associated with a heterologous regulatory sequence that controls gene expression.

174. A recombinant host cell comprising the isolated nucleic acid molecule of claim 165.

175. The recombinant host cell of claim 174 wherein the nucleic acid molecule is operably associated with a heterologous regulatory sequence that controls gene expression.

176. A method for producing a polypeptide, comprising:
(a) culturing a host cell under conditions suitable to produce a polypeptide encoded by the nucleic acid molecule of claim 165; and
(b) recovering the polypeptide from the cell culture.

177. The isolated nucleic acid molecule of claim 1 wherein said first polynucleotide encodes a polypeptide that stimulates B lymphocyte proliferation.

178. The isolated nucleic acid molecule of claim 1 wherein said first polynucleotide encodes a polypeptide that stimulates B lymphocyte differentiation.

179. The isolated nucleic acid molecule of claim 1 wherein said first polynucleotide encodes a polypeptide that stimulates B lymphocyte survival.

180. The isolated nucleic acid molecule of claim 7 wherein the fragment stimulates B lymphocyte survival.

181. The isolated nucleic acid molecule of claim 12 wherein the fragment stimulates B lymphocyte survival.

182. The isolated nucleic acid molecule of claim 56 wherein the polypeptide stimulates B lymphocyte proliferation.

183. The isolated nucleic acid molecule of claim 56 wherein the polypeptide stimulates B lymphocyte differentiation.

184. The isolated nucleic acid molecule of claim 56 wherein the polypeptide stimulates B lymphocyte survival.

185. The isolated nucleic acid molecule of claim 57 wherein the polypeptide stimulates B lymphocyte survival.

186. The isolated nucleic acid molecule of claim 141 wherein the polypeptide stimulates B lymphocyte proliferation.

187. The isolated nucleic acid molecule of claim 141 wherein the polypeptide stimulates B lymphocyte differentiation.

188. The isolated nucleic acid molecule of claim 141 wherein the polypeptide stimulates B lymphocyte survival.

189. The isolated nucleic acid molecule of claim 153 wherein the polynucleotide sequence encodes a polypeptide that stimulates B lymphocyte proliferation.

190. The isolated nucleic acid molecule of claim 153 wherein the polynucleotide sequence encodes a polypeptide that stimulates B lymphocyte differentiation.

191. The isolated nucleic acid molecule of claim 153 wherein the polynucleotide sequence encodes a polypeptide that stimulates B lymphocyte survival.

192. The isolated nucleic acid molecule of claim 22 which consists of a polynucleotide sequence encoding amino acid residues 191 to 284 of SEQ ID NO:2 preceded immediately by an N-terminal methionine.

193. The isolated nucleic acid molecule of claim 192 which consists of nucleotides 717 to 998 of SEQ ID NO:1 preceded immediately by nucleotides 5'-ATG-3'.

194. The isolated nucleic acid molecule of claim 141 wherein the polynucleotide sequence encodes a polypeptide comprising an amino acid sequence that is (a), (b) or (c).

* * * * *

UNITED STATES PATENT AND TRADEMARK OFFICE
CERTIFICATE OF CORRECTION

PATENT NO. : 6,689,579 B2
DATED : February 10, 2004
INVENTOR(S) : Yu et al.

It is certified that error appears in the above-identified patent and that said Letters Patent is hereby corrected as shown below:

Title page,
Item [56], References Cited, OTHER PUBLICATIONS, please insert the following two references:

-- U.S. Patent Application 09/912,293, Rosen, et al., pages 1-75 (pages 1 & 2 partially redacted); portion of Table 2; and SEQ ID NOS:115536 and 197252; and U.S. Patent Application No. 08/971,317, Wiley, SR, published 08/02/01. --

Signed and Sealed this

Eighth Day of June, 2004

JON W. DUDAS
*Acting Director of the United States Patent and Trademark Office*